US012729182B2

(12) United States Patent
Fawaz et al.

(10) Patent No.: US 12,729,182 B2
(45) Date of Patent: Sep. 8, 2026

(54) CRYSTALLINE FORMS OF N,N-DIMETHYLTRYPTAMINE AND METHODS OF USING THE SAME

(71) Applicant: Atai Therapeutics, Inc., Berlin (DE)

(72) Inventors: Majed Fawaz, Foxborough, MA (US); Setu Kasera, Stuttgart (DE)

(73) Assignee: Atai Therapeutics, Inc., New York, NY (US)

( * ) Notice: Subject to any disclaimer, the term of this patent is extended or adjusted under 35 U.S.C. 154(b) by 362 days.

(21) Appl. No.: 18/526,500

(22) Filed: Dec. 1, 2023

(65) Prior Publication Data

US 2024/0199544 A1 Jun. 20, 2024

Related U.S. Application Data

(60) Provisional application No. 63/429,369, filed on Dec. 1, 2022.

(51) Int. Cl.
*C07D 209/16* (2006.01)
*A61K 31/4045* (2006.01)

(52) U.S. Cl.
CPC ........ *C07D 209/16* (2013.01); *A61K 31/4045* (2013.01)

(58) Field of Classification Search
CPC .......................... C07D 209/16; A61K 31/4045
USPC .......................................................... 514/415
See application file for complete search history.

(56) References Cited

U.S. PATENT DOCUMENTS 3,499,003 A 3/1970 Welstead, Jr.
3,594,391 A 7/1971 Wolf et al.
3,781,300 A 12/1973 Wolf et al.
4,252,803 A 2/1981 Webb
5,340,838 A 8/1994 Gidda et al.
5,347,029 A 9/1994 Johnson
5,637,593 A 6/1997 Porter et al.
5,705,527 A 1/1998 Ishihara et al.
6,201,025 B1 3/2001 Dax et al.
6,403,808 B1 6/2002 Glennon et al.
6,436,950 B1 8/2002 Achari et al.
6,500,456 B1 12/2002 Capella
8,268,856 B2 9/2012 Hamann et al.
9,388,395 B2 7/2016 Nazor et al.
9,549,942 B2 1/2017 Jo et al.
10,064,856 B2 9/2018 Bosse et al.
10,550,140 B2 2/2020 Wiles et al.
11,242,318 B2 2/2022 Nivorozhkin et al.
11,292,765 B2 4/2022 Bryson
11,332,441 B2 5/2022 Chadeayne
11,406,619 B2 8/2022 Layzell et al.
11,478,449 B1 10/2022 Witowski et al.
11,591,353 B2 2/2023 Slassi et al.
11,602,521 B2 3/2023 Rao et al.
11,643,391 B2 5/2023 Perni et al.
11,759,452 B2 9/2023 Witowski et al.
12,012,381 B2 6/2024 Perni et al.
12,053,453 B2 8/2024 Witowski et al.
12,065,405 B2 8/2024 Perni
12,128,027 B2 10/2024 Rao et al.
2002/0052370 A1 5/2002 Barber et al.
2002/0115715 A1 8/2002 Dax et al.
2003/0079301 A1 5/2003 Sauter et al.
2004/0235899 A1 11/2004 Maria Assunta et al.
2005/0152858 A1 7/2005 Bertz et al.
2005/0245594 A1 11/2005 Sutter et al.
2005/0250839 A1 11/2005 Marnett et al.
2007/0099909 A1 5/2007 Chen et al.
2007/0140977 A1 6/2007 Yoneto et al.
2008/0248511 A1 10/2008 Daily et al.
2008/0306025 A1 12/2008 Yu et al.
2008/0318957 A1 12/2008 Glinka et al.
2009/0221549 A1 9/2009 Gerber et al.
2010/0113539 A1 5/2010 Scott et al.
2011/0245215 A1 10/2011 Carrara et al.
2012/0028995 A1 2/2012 Ansorge et al.
2012/0108510 A1 5/2012 Young et al.
2012/0122948 A1 5/2012 Soubhye et al.
2015/0071994 A1 3/2015 Schentag et al.
2015/0284365 A1 10/2015 Elder et al.
2015/0346226 A1 12/2015 McConnell et al.
2016/0002195 A1 1/2016 Makriyannis et al.
2016/0074411 A1 3/2016 Krumpl
2016/0106694 A1 4/2016 Roberts et al.

(Continued)

FOREIGN PATENT DOCUMENTS

EP 0821957 A2 2/1998
EP 1336602 A1 8/2003

(Continued)

OTHER PUBLICATIONS

Bergin, "Preliminary X-ray crystallographic study of some psychoactive indole bases," Department of Medical Physics, Feb. 13, 1968, 1 page.

(Continued)

*Primary Examiner* — Kahsay Habte
(74) *Attorney, Agent, or Firm* — COOLEY LLP

(57) ABSTRACT

The present disclosure provides crystalline forms of N,N-dimethyltryptamine,

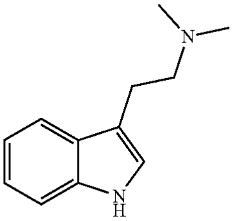

(N,N-DMT)

Also provided herein are methods of using crystalline forms of N,N-DMT and compositions comprising the same, e.g., in the treatment of mental health diseases and/or disorders.

18 Claims, 19 Drawing Sheets

(56) References Cited

U.S. PATENT DOCUMENTS

2016/0303079 A1 10/2016 Hung
2018/0221396 A1 8/2018 Chadeayne
2019/0315689 A1 10/2019 Chen et al.
2019/0345103 A1 11/2019 Batchelor et al.
2020/0199119 A1 6/2020 Thompson et al.
2020/0325124 A1 10/2020 LaVoie et al.
2020/0390746 A1 12/2020 Rands et al.
2020/0397752 A1 12/2020 Perez Castillo et al.
2021/0015738 A1 1/2021 LaRosa et al.
2021/0085671 A1 3/2021 Chadeayne
2021/0108238 A1 4/2021 Protzko
2021/0145851 A1 5/2021 Stamets
2021/0236523 A1 8/2021 Schindler et al.
2021/0277433 A1 9/2021 Protzko
2021/0292278 A1 9/2021 Chadeayne
2021/0322306 A1 10/2021 Espinoza et al.
2021/0322447 A1 10/2021 Plakogiannis et al.
2021/0346347 A1 11/2021 Witowski et al.
2021/0353615 A1 11/2021 Chadeayne
2021/0363104 A1 11/2021 Nivorozhkin et al.
2021/0378969 A1 12/2021 Rands et al.
2021/0395201 A1 12/2021 Rands et al.
2021/0403425 A1 12/2021 Bryson
2022/0015749 A1 1/2022 Sanders et al.
2022/0024956 A1 1/2022 Slassi et al.
2022/0031662 A1 2/2022 Terwey
2022/0071958 A1 3/2022 Terwey
2022/0079881 A1 3/2022 Modi
2022/0096504 A1 3/2022 Blumstock et al.
2022/0259147 A1 8/2022 Feilding-Mellen
2022/0267267 A1 8/2022 Feilding-Mellen
2022/0273628 A1 9/2022 Liechti et al.
2022/0304980 A1 9/2022 Arnold et al.
2022/0339139 A1 10/2022 Rao et al.
2022/0354824 A1 11/2022 Witowski et al.
2022/0388956 A1 12/2022 Short et al.
2023/0041584 A1 2/2023 Perni et al.
2023/0066720 A1 3/2023 Perni et al.
2023/0099972 A1 3/2023 Rao et al.
2023/0136824 A1 5/2023 Rao et al.
2023/0227421 A1 7/2023 Perni et al.
2023/0233537 A1 7/2023 Dornbierer et al.
2023/0310374 A1 10/2023 Rao et al.
2023/0321039 A1 10/2023 Rao et al.
2023/0322735 A1 10/2023 Kruegel
2023/0372295 A1 11/2023 Witowski et al.
2024/0116896 A1 4/2024 Khan et al.
2024/0287107 A1 8/2024 Khan
2024/0400511 A1 12/2024 Perni et al.
2024/0415811 A1 12/2024 Gray
2025/0002457 A1 1/2025 Yacoub et al.
2025/0041273 A1 2/2025 Witowski et al.
2025/0064783 A1 2/2025 Witowski et al.
2025/0163044 A1 5/2025 Banister et al.

FOREIGN PATENT DOCUMENTS

WO WO-9506638 A1 3/1995
WO WO-9524200 A1 9/1995
WO WO-9617842 A1 6/1996
WO WO-0041755 A1 7/2000
WO WO-0051672 A1 9/2000
WO WO-0211800 A2 2/2002
WO WO-02068029 A2 9/2002
WO WO-02068030 A2 9/2002
WO WO-02068031 A2 9/2002
WO WO-02068032 A2 9/2002
WO WO-03000310 A2 1/2003
WO WO-03020350 A1 3/2003
WO WO-03026559 A2 4/2003
WO WO-03082393 A1 10/2003
WO WO-03084591 A1 10/2003
WO WO-03090812 A2 11/2003
WO WO-2006099416 A1 9/2006
WO WO-2006105615 A1 10/2006
WO WO-2010151258 A1 12/2010
WO WO-2011041870 A1 4/2011
WO WO-2013063492 A1 5/2013
WO WO-2018064465 A1 4/2018
WO WO-2018081456 A1 5/2018
WO WO-2018094106 A2 5/2018
WO WO-2018148605 A1 8/2018
WO WO-2019081764 A1 5/2019
WO WO-2019213551 A1 11/2019
WO WO-2020037372 A1 2/2020
WO WO-2020157569 A1 8/2020
WO WO-2020169850 A1 8/2020
WO WO-2020169851 A1 8/2020
WO WO-2020176597 A1 9/2020
WO WO-2020181194 A1 9/2020
WO WO-2020212951 A1 10/2020
WO WO-2021003467 A1 1/2021
WO WO-2021155468 A1 8/2021
WO WO-2021168082 A1 8/2021
WO WO-2021188782 A1 9/2021
WO WO-2021226041 A1 * 11/2021 ........... C07D 209/16
WO WO-2021226416 A1 11/2021
WO WO-2021244831 A1 12/2021
WO WO-2021250434 A1 12/2021
WO WO-2021250435 A1 12/2021
WO WO-2021259962 A1 12/2021
WO WO-2022051670 A1 3/2022
WO WO-2022061242 A1 3/2022
WO WO-2022082058 A1 4/2022
WO WO-2022109050 A1 5/2022
WO WO-2022123232 A1 6/2022
WO WO-2022150675 A1 7/2022
WO WO-2022160056 A1 8/2022
WO WO-2022170442 A1 8/2022
WO WO-2022195011 A1 9/2022
WO WO-2022232179 A1 11/2022
WO WO-2022235514 A1 11/2022
WO WO-2022235529 A1 11/2022
WO WO-2022243285 A1 11/2022
WO WO-2022246572 A1 12/2022
WO WO-2022251351 A1 12/2022
WO WO-2022261383 A1 12/2022
WO WO-2023283386 A2 1/2023
WO WO-2023021112 A1 2/2023
WO WO-2023036473 A1 3/2023
WO WO-2023055992 A1 4/2023
WO WO-2023076135 A1 5/2023
WO WO-2023076150 A1 5/2023
WO WO-2023078604 A1 5/2023
WO WO-2023111544 A2 6/2023
WO WO-2023115166 A1 6/2023
WO WO-2023129956 7/2023
WO WO-2024054866 A2 3/2024
WO WO-2024092106 A2 5/2024
WO WO-2024118767 A2 6/2024
WO WO-2024119075 A1 6/2024
WO WO-2024130140 A2 6/2024
WO WO-2024130140 A3 7/2024
WO WO-2024227149 A2 10/2024
WO WO-2024243488 A2 11/2024
WO WO-2025019800 A1 1/2025
WO WO-2025024637 A1 1/2025
WO WO-2025054397 A1 3/2025
WO WO-2025076151 A1 4/2025
WO WO-2025137581 A1 6/2025

OTHER PUBLICATIONS

Falkenberg, "The Crystal and Molecular Structure of (N,N)-Dimethyltryptamine," Acta Cryst, Mar. 9, 1972, 9 pages.

Gaujac et al., "Investigations into the polymorphic properties of N, N-dimethyltryptamine by X-ray diffraction and differential scanning calorimetry," Microchemical Journal 110, Mar. 2, 2013, 12 pages.

Abiero et al., "Four Novel Synthetic Tryptamine Analogs Induce Head-Twitch Responses and Increase 5-HTR2a in the Prefrontal Cortex in Mice." Biomol Ther (Seoul). Jan. 1, 2020; 28(1): 83-91.

(56) References Cited

OTHER PUBLICATIONS

Andersson et al., “Psychoactive substances as a last resort—a qualitative study of self-treatment of migraine and cluster headaches.” Harm Reduct J. Sep. 5, 2017; 14(1): 60. 11 pages.
Archer et al., “5-Methoxy-N, N-dimethyltryptamine-induced analgesia is blocked by alpha-adrenoceptor antagonists in rats.” Br J Pharmacol. Oct. 1986;89(2):293-8. doi: 10.1111/j.1476-5381.1986.tb10259.x.
Baker et al., “Neurochemical and neuropharmacological investigation of N-cyanoethyltryptamine, a potential prodrug of tryptamine.” Proc West Pharmacol Soc., 1987; 30: 307-11.
Baker et al., “Neuropharmacological and Neurochemical Properties of N-(2-Cyanoethyl)-2-Phenylethylamine, A Prodrug of 2-Phenylethylamine.” Br J Pharmacol. Oct. 1987; 92(2): 243-55.
Banker, G. S., et al., “Prodrugs.” Modern Pharmaceutics, Third Edition, Revised, and Expanded, Marcel Dekker, Inc. (1996); pp. 451 and 596; 3 pages.
Barker, “Administration of N,N-dimethyltryptamine (DMT) in psychedelic therapeutics and research and the study of endogenous DMT.” Psychopharmacology (Berl). Jun. 2022; 239(6): 1749-1763. Epub Jan. 22, 2022, with erratum, 16 pages.
Barker, “N, N-Dimethyltryptamine (DMT), an Endogenous Hallucinogen: Past, Present, and Future Research to Determine Its Role and Function.” Front Neurosci. Aug. 6, 2018:12:536. doi: 10.3389/fnins.2018.00536. eCollection 2018. 17 pages.
Barsuglia et al., “Intensity of mystical experiences occasioned by 5-MeO-DMT and comparison with a prior psilocybin study.” Front Psychol. Dec. 6, 2018: 9: 2459. doi: 10.3389/fpsyg.2018.02459. eCollection 2018. 6 pages.
Benneyworth et al., “Complex discriminative stimulus properties of (+)lysergic acid diethylamide (LSD) in C57Bl/6J mice.” Psychopharmacology (2005) 179, 854-862.
Berge et al., “Pharmaceutical salts”, Journal of Pharmaceutical Sciences (Jan. 1977); 66(1): 1-19. doi: 10.1002/jps.2600660104.
Bergin, “The structure of the catecholamines. II. The crystal structure of dopamine hydrochloride.” Acta Crystallogr B Struct Crystallogr Cryst Chem. Nov. 15, 1968;24(11):1506-10. doi: 10.1107/s0567740868004553.
Bibi et al., “Use of Permeapad® for prediction of buccal absorption: A comparison to in vitro, ex vivo and in vivo method.” Eur J Pharm Sci. Oct. 10, 2016:93:399-404. doi:10.1016/j.ejps.2016.08.041. Epub Aug. 24, 2016.
Blough, B. E., et al., “Alpha-ethyltryptamines as dual dopamine-serotonin releasers.” Bioorganic & Medicinal Chemistry Letters (2014); 24(19): 4754-4758. doi: 10.1016/j.bmcl.2014.07.062. Epub Jul. 29, 2014.
Brandt et al., “Analytical methods for psychoactive N,N-dialkylated tryptamines.” Trends in Analytical Chemistry, vol. 29, No. 8, 2010, pp. 858-869.
Brandt et al., “Characterization of the synthesis of N,N-dimethyltryptamine by reductive amination using gas chromatography ion trap mass spectrometry.” Drug Test Anal. Jul. 2010; 2(7): 330-8. doi: 10.1002/dta.142.
Brito-Da-Costa, et al., “Toxicokinetics and toxicodynamics of ayahuasca alkaloids N, N-dimethyltryptamine (DMT), harmine, harmaline and tetrahydroharmine: clinical and forensic impact.” Pharmaceuticals (Basel). Oct. 23, 2020; 13(11): 334. doi: 10.3390/ph13110334. 36 pages.
Buchwald, Peter, “Soft drugs: design principles, success stories, and future perspectives.” Expert Opin Drug Metab Toxicol. Aug. 2020; 16(8): 645-650. Epub Jun. 20, 2020.
Bugaenko et al., “Synthesis of indoles: recent advances.” Russ. Chem. Rev., 2019, 88 (2)99-159, 62 pages.
Cameron et al., “A non-hallucinogenic psychedelic analogue with therapeutic potential.” Nature. Jan. 2021;589(7842):474-479. doi: 10.1038/s41586-020-3008-z. Epub Dec. 9, 2020, and Reporting Summary, 24 pages.
Cameron et al., “Chronic, Intermittent Microdoses of the Psychedelic N , N-Dimethyltryptamine (DMT) Produce Positive Effects on Mood and Anxiety in Rodents.” ACS Chemical Neuroscience, vol. 10, No. 7, Jul. 17, 2019 (Jul. 17, 2019), pp. 3261-3270.
Cameron et al., “Effects of N,N-Dimethyltryptamine on Rat Behaviors Relevant to Anxiety and Depression.” ACS Chem Neurosci, Jul. 18, 2018; 9(7): 1582-1590. Epub Apr. 24, 2018.
Carhart-Harris et al., “The therapeutic potential of psychedelic drugs: past, present, and future”, Neuropsychopharmacology (2017); 42(11): 2105-2113. doi: 10.1038/npp.2017.84. Epub Apr. 26, 2017.
Carhart-Harris, “Psilocybin for treatment-resistant depression: fMRI-measured brain mechanisms.” Sci Rep. Oct. 13, 2017; 7(1): 13187. doi: 10.1038/s41598-017-13282-7. 11 pages.
Carter et al., “Modulating the rate and rhythmicity of perceptual rivalry alternations with the mixed 5-HT2A and 5-HT1A agonist psilocybin.” Neuropsychopharmacology (2005); 30(6): 1154-1162. doi: 10.1038/sj.npp.1300621.
Carvalho et al., “Mucoadhesive drug delivery systems,” BJPS, vol. 46, n. 1, Jan./Mar. 2010. 18 pages.
CAS Registry No. 1152718-19-8, Benzenemethanamine, N-[4-(1,1-dimethylethyl)cyclohexyl]-2,4-difluoro-α-methyl-, Jun. 5, 2009, 1 page.
CAS Registry No. 1152826-22-6, Benzenemethanamine, 5-bromo-N-[4-(1,1-dimethylpropyl)cyclohexyl]-2-fluoro-, Jun. 7, 2009, 1 page.
CAS Registry No. 1154138-59-6, Benzenemethanamine, N-[4-(1,1-dimethylpropyl)cyclohexyl]-2,5-difluoro-, Jun. 9, 2009, 1 page.
CAS Registry No. 127456-43-3, Phenol, 2-[[[4-(1,1-dimethylethyl)cyclohexyl]amino]methyl]-4-(1,1-dimethylpropyl)-, trans-(9CI), Jun. 1, 1990, 1 page.
CAS Registry No. 127456-44-4, 1H-Inden-5-ol, 6-[[[4-(1,1-dimethylethyl)cyclohexyl]amino]methyl]-2,3-dihydro-, trans-(9CI), Jun. 1, 1990, 1 page.
CAS Registry No. 127456-45-5, Phenol, 4-(1,1-dimethylethyl)-2-[[[4-(1,1-dimethylethyl)cyclohexyl]amino]methyl]-, trans-(9CI), Jun. 1, 1990, 1 page.
CAS Registry No. 127456-46-6, Phenol, 4-(1,1-dimethylethyl)-2-[[[4-(1,1-dimethylethyl) cyclohexyl]amino]methyl]-6-methyl-, hydrochloride, trans-(9CI), Jun. 1, 1990, 1 page.
CAS Registry No. 127456-52-4, Phenol, 2-[[[4-(1,1-dimethylethyl)cyclohexyl]amino]methyl]-4-(1-methylethyl)-, cis-(9CI), Jun. 1, 1990, 1 page.
CAS Registry No. 127456-56-8, Phenol, 4-chloro-2-[[[4-(1,1-dimethylethyl)cyclohexyl]amino]methyl]-, trans-(9CI), Jun. 1, 1990, 1 page.
CAS Registry No. 127456-57-9, Phenol, 2-[[[4-(1,1-dimethylethyl)cyclohexyl]amino]methyl]-4-fluoro-, trans-(9CI), Jun. 1, 1990, 2 pages.
CAS Registry No. 1308467-14-2, 1,2-Benzenediol, 3-[[[4-(1,1-dimethylpropyl)cyclohexyl]amino]methyl]-, Jun. 10, 2011, 1 page.
CAS Registry No. 1405571-87-0, Benzenemethanamine, 2-bromo-N-[4-(1,1-dimethylpropyl)cyclohexyl]-5-fluoro-, Nov. 23, 2012, 1 page.
CAS Registry No. 1406541-63-6, Phenol, 2-chloro-4-[[[4-(1,1-dimethylpropyl)cyclohexyl]amino]methyl]-, Nov. 25, 2012, 1 page.
CAS Registry No. 1411655-23-6, Benzenemethanamine, N-[4-(1,1-dimethylpropyl)cyclohexyl]-2,3-difluoro-, Dec. 5, 2012, 1 page.
CAS Registry No. 1456349-79-3, Benzenemethanamine, 2,3-dichloro-N-[4-(1,1-dimethylpropyl)cyclohexyl]-, Oct. 6, 2013, 1 page.
CAS Registry No. 1458497-71-6, Benzenemethanamine, 2,4-dichloro-N-[4-(1,1-dimethylethyl)cyclohexyl]-α-methyl-, Oct. 15, 2013, 1 page.
CAS Registry No. 1459328-13-2, Phenol, 2-bromo-4-[[[4-(1,1-dimethylpropyl)cyclohexyl]amino]methyl]-, Oct. 16, 2013, 1 page.
CAS Registry No. 1490220-45-5, Benzenemethanamine, 2-bromo-5-chloro-N-[4-(1,1-dimethylpropyl)cyclohexyl]-, Dec. 8, 2013, 1 page.
CAS Registry No. 1515984-46-9, Benzamide, N-(4-aminocyclohexyl)-3-chloro-N,5-dimethyl-, Jan. 10, 2014, 1 page.
CAS Registry No. 1542027-51-9, Phenol, 3-chloro-2-[[[4-(1,1-dimethylpropyl)cyclohexyl]amino]methyl]-, Feb. 11, 2014, 1 page.
CAS Registry No. 1624268-56-9, Benzamide, 4-[[[4-(1,1-dimethylethyl)cyclohexyl]amino]methyl]-N-methyl-, Sep. 22, 2014, 1 page.

(56) References Cited

OTHER PUBLICATIONS

CAS Registry No. 1712122-27-4, Benzenemethanamine, 5-chloro-N-[4-(1,1-dimethylpropyl)cyclohexyl]-2-fluoro-, May 25, 2015, 1 page.
CAS Registry No. 1772618-27-5, Phenol, 3-[[[4-(1,1-dimethylpropyl)cyclohexyl]amino]methyl]-5-fluoro-, Jun. 3, 2015, 1 page.
CAS Registry No. 1775706-37-0, Phenol, 2-chloro-6-[[[4-(1,1-dimethylpropyl)cyclohexyl]amino]methyl]-, Jun. 8, 2015, 1 page.
CAS Registry No. 1858436-76-6, Bicyclo[3.1.0]hexan-2-amine, N-[(3-chloro-5-methylphenyl)methyl]-, Feb. 3, 2016, 1 page.
CAS Registry No. 1931388-10-1, Benzenemethanamine, 2,5-dichloro-N-[4-(1,1-dimethylpropyl)cyclohexyl]-, Jun. 14, 2016, 1 page.
CAS Registry No. 1939264-55-7, Phenol, 4-[[[4-(1,1-dimethylpropyl)cyclohexyl]amino]methyl]-2-fluoro-, Jun. 26, 2016, 1 page.
CAS Registry No. 1939792-99-0, Benzenemethanamine, 5-bromo-2-chloro-N-[4-(1,1-dimethylpropyl)cyclohexyl]-, Jun. 27, 2016, 1 page.
CAS Registry No. 1962333-15-8, Benzenemethanamine, N-[4-(1,1-dimethylpropyl)cyclohexyl]-5-fluoro-2-methyl-, Jul. 29, 2016, 1 page.
CAS Registry No. 2032268-58-7, Cyclohexanecarboxylic acid, 4-[[(3-chloro-5-methylphenyl)methyl]amino]-, Nov. 15, 2016, 1 page.
CAS Registry No. 2107153-36-4, 1H-Indole-3-ethanamine, 2-chloro-4-methoxy-N-methyl-, Aug. 2, 2017, 3 pages.
CAS Registry No. 2199998-08-6, Cyclohexanecarboxylic acid, 2-[[(3-chloro-5-methylphenyl)methyl]amino]-1-methyl-, Mar. 27, 2018, 1 page.
CAS Registry No. 2202151-69-5, Cyclohexanecarboxylic acid, 3-[[(3-chloro-5-methylphenyl)methyl]amino]-, Mar. 30, 2018, 1 page.
CAS Registry No. 2322790-81-6, Benzenemethanamine, N-[4-(1,1-dimethylethyl)cyclohexyl]-3-(trifluoromethyl)-, Jun. 2, 2019, 1 page.
CAS Registry No. 2419600-39-6, Benzenemethanamine, 3-chloro-N-[4-(1,1-dimethylpropyl)cyclohexyl]-5-methyl-, Jun. 5, 2020, 1 page.
CAS Registry No. 415970-94-4, Benzenemethanamine, N-[4-(1,1-dimethylethyl)cyclohexyl]-3,5-dimethoxy-, May 15, 2002, 1 page.
CAS Registry No. 744981-83-7, Phenol, 2,6-dibromo-4-[[[4-(1,1-dimethylethyl)cyclohexyl]amino]methyl]-, Sep. 15, 2004, 1 page.
CAS Registry No. 793633-39-3, Phenol, 4-(1,1-dimethylethyl)-2-[[[trans-4-(1,1-dimethylethyl)cyclohexyl]amino]methyl]-6-methyl-, Dec. 6, 2004, 1 page.
Cayman Chemical "Safety Data Sheet Acc. to OSHA HCS", N,N-DMT (Succinate), CAS No. 2853570-32-6, Cayman Chemical: pp. 1-7, Revised Feb. 15, 2024.
Cayman Chemical, "Safety Data Sheet", Caymanchem.com, Apr. 21, 2021, [online] available at: https://cdn.caymanchem.com/cdn/msds/33586m.pdf. 6 printed pages.
Cayman Chemical, product information for Item No. 33586, "N,N-DMT (succinate)." Apr. 26, 2021, 1 page.
Chadeayne, Andrew R. et al., "The Crystal Structure of 4-AcO-DMT Fumarate." Psychedelic Science Review, Science Review Team, Mar. 25, 2019, online at: https://psychedelicreview.com/the-crystal-structure-of-4-aco-dmt-fumarate/, 11 pages.
Chegaev, et al., "No-donor melatonin derivatives: synthesis and in vitro pharmacological characterization", J Pineal Res. Apr. 2007; 42(4): 371-85.
Chen, et al., "Structure-activity relationships in a series of 5-[(2, 5-dihydroxybenzyl) amino] salicylate inhibitors of EGF-receptor-associated tyrosine kinase: importance of additional hydrophobic aromatic interactions." J Med Chem. Mar. 18, 1994;37(6):845-59. doi: 10.1021/jm00032a020.
ClinicalTrials.gov, "Effects of Dimethyltryptamine in Healthy Subjects (DMT)", Apr. 20, 2020, 9 pages. Retrieved on Jun. 24, 2022 from https://clinicaltrials.gov/ct2/show/NCT04353024.
Cocchi et al., "Novel Psychoactive Phenethylamines: Impact on Genetic Material." Int J Mol Sci. Dec. 17, 2020; 21(24): 9616. doi: 10.3390/ijms21249616. 17 pages.
Corne et al., "A possible correlation between drug-induced hallucinations in man and a behavioural response in mice", Psychopharmacologia (Berl.) (1967); 11: 65-78. doi: 10.1007/BF00401509.
Cozzi, Nicholas V. et al., "Synthesis and characterization of high-purity N,N-dimethyltryptamine hemifumarate for human clinical trials." Drug Test Anal. Oct. 2020; 12(10): 1483-1493. doi: 10.1002/dta.2889. Epub Jul. 14, 2020.
Daiber et al., "Organic Nitrate Therapy, Nitrate Tolerance, and Nitrate-Induced Endothelial Dysfunction: Emphasis on Redox Biology and Oxidative Stress." Antioxid Redox Signal. Oct. 10, 2015;23(11):899-942.).
Dakic et al., "Short term changes in the proteome of human cerebral organoids induced by 5-MeO-DMT." Sci Rep. Oct. 9, 2017;7(1):12863. doi: 10.1038/s41598-017-12779-5. 13 pages.
Dalgleish, T., et al., "Transdiagnostic Approaches to Mental Health Problems: Current Status and Future Directions." Journal of Consulting and Clinical Psychology, 2020, vol. 88, No. 3, 179-195.
Davis et al., "5-methoxy-N, N-dimethyltryptamine (5-MeO-DMT) used in a naturalistic group setting is associated with unintended improvements in depression and anxiety." Am J Drug Alcohol Abuse. 2019; 45(2): 161-169. doi: 10.1080/00952990.2018.1545024. Epub Mar. 1, 2019. 10 pages.
Davis, et al., "The epidemiology of 5-methoxy-N, N-dimethyltryptamine (5-MeO-DMT) use: Benefits, consequences, patterns of use, subjective effects, and reasons for consumption." J Psychopharmacol, Jul. 2018. vol. 2, Issue 7, Epub Apr. 30, 2018. 14 pages.
De Barros et al., "Synthesis of 25X-BOMes and 25X-NBOHs (X=H, I, Br) for pharmacological studies and as reference standards for forensic purposes." Tetrahedron Letters 66 (2021) 152804, 4 pages.
Declaration of Majed Fawaz under 37 C.F.R. § 1.130, in U.S. Appl. No. 17/824,861, dated Jun. 2024, 2 pages.
Dimoitou, "Nasal spray" #3 Posted : Jun. 27, 2014 6:58:57 pm DMT-Nexus, Jun. 27, 2014, https://forum.dmt-nexus.me/threads/nasal-spray.343226/. 5 pages.
Du, M., "An Overview on Transmucosal Permeability and Formulation." J Develop Drugs. 13:227, (2024), 2 pages.
Dunlap et al., "Identification of psychoplastogenic N, N-dimethylaminoisotryptamine (isoDMT) analogues through structure-activity relationship studies." J Med Chem Feb. 13, 2020; 63(3): 1142-1155. Epub Jan. 24, 2020. 14 pages.
Dunlap, Lee, E. et al., Reaction of N,N-Dimethyltryptamine with Dichloromethane Under Common Experimental Conditions, ACS Omega, 2018, 3, 4968-4973.
Durham and Russo, "Regulation of calcitonin gene-related peptide secretion by a serotonergic antimigraine drug." J Neurosci. May 1, 1999; 19(9): 3423-9. doi: 10.1523/JNEUROSCI.19-09-03423.1999.
Extended European Search Report for EP Application No. 21800237.6, dated Apr. 15, 2024, 8 pages.
Extended European Search Report for EP Application No. 22796577.9, dated Mar. 10, 2025, 10 pages.
Extended European Search Report for EP Application No. 22812068.9, dated Mar. 28, 2025, 13 pages.
Extended European Search Report for European Application No. 22821070.4 mailed May 26, 2025, 11 pages.
Extended European Search Report for European Application No. 22877368.5 mailed Jun. 16, 2025, 9 pages.
Gaujac et al. "Determination of N,N-dimethyltryptamine in beverages consumed in religious practices by headspace solid-phase microextraction followed by gas chromatography ion trap mass spectrometry," Talanta. Mar. 15, 2013: 106:394-8. doi: 10.1016/j.talanta.2013.01.017. Epub Feb. 1, 2013.
Glatfelter G, et al., "Synthesis, Structural Characterization, and Pharmacological Activity of Novel Quaternary Salts of 4-Substituted Tryptamines", ACS Omega, Jul. 2022, vol. 7(28), pp. 24888-24894.
Glennon et al., "Hallucinogens as discriminative stimuli: A comparison of 4-OMe and 5-OMe DMT with their methylthio counterparts", Life Science, Pergamon Press, Oxford, GB, vol. 30, No. 5, Feb. 1, 1982 (Feb. 1, 1982), pp. 465-467, XP023723306, ISSN: 0024-3205, DOI: 10.1016/0024-3205(82)90463-5 [retrieved on Feb. 1, 1982].

(56) References Cited

OTHER PUBLICATIONS

Glennon et al., "Influence of amine substituents on 5-HT2A versus 5-HT2C binding of phenylalkyl- and indolylalkylamines." J Med Chem. Jun. 24, 1994; 37(13): 1929-35. doi: 10.1021/jm00039a004.
Glennon et al., "Synthesis and evaluation of a novel series of N,N-dimethylisotryptamines", J Med Chem. Jan. 1984; 27(1): 41-5.
Gonzalez-Maeso et al., "Hallucinogens Recruit Specific Cortical 5-HT2A Receptor-Mediated Signaling Pathways to Affect Behavior," Neuron, Feb. 2007, 53, 439-452.
Graeff F.G., et al., "Role of 5-HT in stress, anxiety and depression", Pharmacology Biochemistry and Behavior, Elsevier, US, vol. 54, No. 1, Jan. 1, 1996 (Jan. 1, 1996), pp. 129-141.
Gribble, "Recent developments in indole ring synthesis-methodology and applications", Journal of the Chemical Society, Perkin Transactions, 2000, pp. 1045-1075.
Griffiths et al., "Psilocybin produces substantial and sustained decreases in depression and anxiety in patients with life-threatening cancer: a randomized double-blind trial", Journal of Psychopharmacology (2016); 30: 1181-1197. doi: 10.1177/0269881116675513.
Grundke et al., "Photochemical α-Aminonitrile Synthesis Using Zn-Phthalocyanines as Near-Infrared Photocatalysts", J Org Chem. May 6, 2022; 87(9): 5630-5642, with supporting info. Epub Apr. 14, 2022. 60 pages.
Gurevich and Gurevich, "GPCR Signaling Regulation: The Role of GRKs and Arrestins", Front Pharmacol. Feb. 19, 2019: 10: 125. eCollection 2019, 11 pages.
Gyermek L., "A New Class of 5-Hydroxytryptamine Antagonists", Journal of Medicinal Chemistry, vol. 7, Jan. 1, 1964 (Jan. 1, 1964), pp. 280-282.
Halberstadt, A. L., "Recent Advances in the Neuropsychopharmacology of Serotonergic Hallucinogens." Behav Brain Res. Jan. 15, 2015: 277: 99-120. doi: 10.1016/j.bbr.2014.07.016. Epub Jul. 15, 2014.
Halberstadt et al., "Differential contributions of serotonin receptors to the behavioral effects of indoleamine hallucinogens in mice", J Psychopharmacol. Nov. 2011; 25(11): 1548-61. Epub Dec. 8, 2010.
Hamada et al., "Water-soluble prodrugs of dipeptide HIV protease inhibitors based on O?N intramolecular acyl migration: Design, synthesis and kinetic study" Bioorg Med Chem. Jan. 2, 2004;12(1):159-70. doi: 10.1016/j.bmc.2003.10.026.
Hansen et al., "Synthesis and pharmacological evaluation of N-benzyl substituted 4-bromo-2,5-dimethoxyphenethylamines as 5-HT2A/2C partial agonists." Bioorganic & Medicinal Chemistry 23 (2015), 3933-3937.
Hansen et al., "Synthesis and Structure-Activity Relationships of N-Benzyl Phenethylamines as 5-HT2A/2C Agonists." ACS Chem Neurosci. Mar. 19, 2014;5(3):243-9. doi: 10.1021/cn400216u. Epub Jan. 15, 2014.
Harriott et al., "Animal models of migraine and experimental techniques used to examine trigeminal sensory processing", J Headache Pain. Aug. 29, 2019; 20(1): 91. 15 pages.
Hart et al., "Melting Point Determination, Melting Range", Adapted from Organic Chemistry: A Short course, 13th ed. Houghton-Mifflin, Boston, 2012, available at: https://chemistry.sites.clemson.edu/organic/Labs/2270Docs/MeltingPoint.pdf, 4 pages.
Hasegawa et al., "A Novel Methodology for Preparing 5-chloro- and 5-bromo-tryptamines and tryptophans, and its Application to the Synthesis of (+/−)- bromochelonin BI." (1999), Heterocycles, vol. 51, No. 12, pp. 2815-2821.
Holze et al. "Distinct acute effects of LSD, MDMA, and Damphetamine in healthy subjects." Neuropsychopharmacology. Feb. 2020;45(3):462-471.
Huang et al., "Nose-to-brain delivery of drug nanocrystals by using Ca2+ responsive deacetylated gellan gum based in situ-nanogel." International Journal of Pharmaceuticals. 2020;S0378-5173(20)31167-4. 41 pages.
Humphrey et al., "Practical methodologies for the synthesis of indoles", Chem Rev. Jul. 2006; 106(7): 2875-911, 37 pages.
Huttunen, et al., "Prodrugs-from Serendipity to Rational Design", Pharmacological Reviews, vol. 63, No. 3, Sep. 2011, pp. 750-771.
International Preliminary Report on Patentability for International Application No. PCT/US2022/026396, mailed Nov. 9, 2023, 8 pages.
International Preliminary Report on Patentability for International Application No. PCT/US2022/030912, mailed Dec. 7, 2023, 10 pages.
International Preliminary Report on Patentability for International Application No. PCT/US2022/032918, mailed Dec. 21, 2023, 7 pages.
International Preliminary Report on Patentability for International Application No. PCT/US2022/045336, mailed Apr. 11, 2024, 7 pages.
International Preliminary Report on Patentability for International Application No. PCT/US2022/047520, mailed May 10, 2024, 8 pages.
International Preliminary Report on Patentability for International Application No. PCT/US2023/073574, mailed Mar. 20, 2025, 9 pages.
International Preliminary Report on Patentability for International Application No. PCT/US2023/084319 mailed Jun. 26, 2025, 9 pages.
International Preliminary Report on Patentability for PCT Application No. PCT/US2023/077879 mailed May 8, 2025, 9 pages.
International Preliminary Report on Patentability for PCT Application No. PCT/US2023/082080 mailed Jun. 12, 2025, 7 pages.
International Search Report and Written Opinion for International Application No. PCT/US2021/031215, mailed Oct. 1, 2021, 10 pages.
International Search Report and Written Opinion for International Application No. PCT/US2022/026396, mailed Jul. 28, 2022, 10 pages.
International Search Report and Written Opinion for International Application No. PCT/US2022/030912, mailed Oct. 5, 2022, 20 pages.
International Search Report and Written Opinion for International Application No. PCT/US2022/032918, mailed Oct. 12, 2022, 10 pages.
International Search Report and Written Opinion for International Application No. PCT/US2022/045336, mailed Jan. 13, 2023, 14 pages.
International Search Report and Written Opinion for International Application No. PCT/US2022/047520, mailed Mar. 1, 2023, 11 pages.
International Search Report and Written Opinion for International Application No. PCT/US2022/082465, mailed Jun. 6, 2023, 11 pages.
International Search Report and Written Opinion for International Application No. PCT/US2023/073574, mailed Feb. 16, 2024, 13 pages.
International Search Report and Written Opinion for International Application No. PCT/US2023/077879, mailed Apr. 4, 2024, 11 pages.
International Search Report and Written Opinion for International Application No. PCT/US2023/082080, mailed Apr. 4, 2024, 8 pages.
International Search Report and Written Opinion for International Application No. PCT/US2023/084319, mailed May 20, 2024, 13 pages.
International Search Report and Written Opinion for International Application No. PCT/US2024/026797, mailed Sep. 6, 2024, 10 pages.
International Search Report and Written Opinion for International Application No. PCT/US2024/038804, mailed Dec. 17, 2024, 14 pages.
International Search Report and Written Opinion for International Application No. PCT/US2024/039503, mailed Nov. 5, 2024, 17 pages.
International Search Report and Written Opinion for International Application No. PCT/US2024/045494, mailed Nov. 15, 2024, 11 pages.
International Search Report and Written Opinion for International Application No. PCT/US2024/049678, mailed Jan. 21, 2025, 9 pages.

(56) References Cited

OTHER PUBLICATIONS

International Search Report and Written Opinion for International Application No. PCT/US2025/014571, mailed Mar. 21, 2025, 15 pages.
International Search Report and Written Opinion for PCT Application No. PCT/US2024/061478 mailed Apr. 23, 2025, 10 pages.
Invitation to Pay Additional Fees for International Application No. PCT/US2022/030912, mailed Jul. 28, 2022, 8 pages.
Invitation to Pay Additional Fees for International Application No. PCT/US2022/032918, mailed Aug. 12, 2022, 2 pages.
Invitation to Pay Additional Fees for International Application No. PCT/US2022/082465, mailed Mar. 16, 2023, 3 pages.
Invitation to Pay Additional Fees for International Application No. PCT/US2023/073574, mailed Nov. 6, 2023, 2 pages.
Invitation to Pay Additional Fees for International Application No. PCT/US2024/026797, mailed Jun. 25, 2024, 2 pages.
Invitation to Pay Additional Fees for International Application No. PCT/US2024/038804, mailed Sep. 23, 2024, 3 pages.
Invitation to Pay Additional Fees for International Application No. PCT/US2024/039503, mailed Sep. 10, 2024, 2 pages.
Invitation to Pay Additional Fees for International Application No. PCT/US2024/061478, mailed Feb. 25, 2025, 2 pages.
Invitation to Pay Additional Fees for International Application No. PCT/US22/47520, mailed Jan. 3, 2023, 2 pages.
Invitation to Pay Additional fees for PCT Application No. PCT/US2025/026640, mailed Jun. 24, 2025, 2 pages.
Kaminska et al., "25C-NBOMe short characterization." Forensic Toxicology (2020) 38:490-495 https://doi.org/10.1007/s11419-020-00530-1.
Klein et al., "Toward selective drug development for the human 5-hydroxytryptamine 1E receptor: a comparison of 5-hydroxytryptamine 1E and 1F receptor structure-affinity relationships", J Pharmacol Exp Ther. Jun. 2011; 337(3): 860-7. Epub Mar. 21, 2011.
Kline et al, "Structure-activity relationships in potentially hallucinogenic N, N-dialkyltryptamines substituted in the benzene moiety." J Med Chem. Aug. 1982; 25(8): 908-13. doi: 10.1021/jm00350a005.
Kraehenmann et al., "Dreamlike effects of LSD on waking imagery in humans depend on serotonin 2A receptor activation", Psychopharmacology (Berl) (2017); 234: 2031-2046. doi: 10.1007/s00213-017-4610-0. Epub Apr. 7, 2017.
Kraehenmann et al., "LSD Increases Primary Process Thinking via Serotonin 2A Receptor Activation", Frontiers in Pharmacology (2017); 8: 814; 9 pages. doi: 10.3389/fphar.2017.00814.
Krise, J. P., et al., "Novel prodrug approach for tertiary amines: synthesis and preliminary evaluation of N-phosphonooxymethyl prodrugs", J Med Chem. Aug. 12, 1999; 42(16): 3094-100.
Kucklander, et al., "Darstellung und Oxidation von 2-(2, 5-Dihydroxy-phenyl)-ethylamin-Derivaten, II/Synthesis and Oxidation of 2-(2, 5-Dihydroxyphenyl)-ethylamine Derivatives, II", Zeitschrift für Naturforschung B, 1987, pp. 1567-1577 (with English abstract). 12 pages.
Lambert et al., "Looking in the Wrong Place? The Search for an Ideal Migraine Preventative." Drug Development Research, 20071218 New York, NY, US—ISSN 0272-4391, vol. 68, No. 6, pp. 376-388. http://dx.doi.org/10.1002/ddr.20204.
Li et al., "Treatment of breast and lung cancer cells with a N-7 benzyl guanosine monophosphate tryptamine phosphoramidate pronucleotide (4Ei-1) results in chemosensitization to gemcitabine and induced elF4E proteasomal degradation." Mol Pharm., Feb. 2013, pp. 523-531.
Lima da Cruz et al., "Corrigendum: A Single Dose of 5-MeO-DMT Stimulates Cell Proliferation, Neuronal Survivability, Morphological and Functional Changes in Adult Mice Ventral Dentate Gyrus." Front Mol Neurosci. Sep. 4, 2018:11:312. doi: 10.3389/fnmol.2018.00312. eCollection 2018. 11 pages.
Lyon et al., "3, 4-Methylenedioxymethamphetamine (MDMA): stereoselective interactions at brain 5-HT1 and 5-HT2 receptors." Psychopharmacology (1986); 88: 525-526. doi: 10.1007/BF00178519.
Lyon et al., "Indolealkylamine analogs share 5-HT2 binding characteristics with phenylalkylamine hallucinogens", European Journal of Pharmacology, 1988, pp. 291-297.
Madhav, et al., "Orotransmucosal drug delivery systems: A review", Journal of Controlled Release (Nov. 16, 2009); 140(1): 2-11. doi:10.1016/j.jconrel.2009.07.016. Epub Aug. 6, 2009.
Madsen et al., "Psilocybin-induced reduction in chronic cluster headache attack frequency correlates with changes in hypothalamic functional connectivity", medRxiv. Jul. 10, 2022: Jul. 2022.
Madsen et al., "Psychedelic effects of psilocybin correlate with serotonin 2A receptor occupancy and plasma psilocin levels," Neuropsychopharmacology (2019) 44: 1328-1334.
Mahalingam, "Semisolid Dosages: Ointments, Creams, and Gels." in Pharmaceutical Manufacturing Handbook: Production and Processes. (Chapter 9, 267-312), Shayne C. Gad ed., John Wiley & Sons, Inc. 2008.
Malaca, S., et al., "Toxicology and Analysis of Psychoactive Tryptamines." Int J Mol Sci. Dec. 4, 2020; 21(23): 9279. doi: 10.3390/ijms21239279. 30 pages.
McBride, "Bufotenine: Toward an Understanding of Possible Psychoactive Mechanisms", Journal of Psychoactive Drugs, Jul.-Sep. 2000, pp. 321-331.
Mcclure-Begley and Roth, "The promises and perils of psychedelic pharmacology for psychiatry", Nat Rev Drug Discov. Jun. 2022; 21(6): 463-473. Epub Mar. 17, 2022.
Mertens and Preller, "Classical Psychedelics as Therapeutics in Psychiatry—Current Clinical Evidence and Potential Therapeutic Mechanisms in Substance Use and Mood Disorders", Pharmacopsychiatry. Jul. 2021; 54(4): 176-190. Epub Jan. 20, 2021.
Milne et al., "Metabolic engineering of *Saccharomyces cerevisiae* for the de novo production of psilocybin and related tryptamine derivatives." Metab Eng. Jul. 2020:60:25-36. doi: 10.1016/j.ymben.2019.12.007. Epub Mar. 26, 2020.
Mithoefer et al., "The safety and efficacy of±3, 4-methylenedioxymethamphetamine-assisted psychotherapy in subjects with chronic, treatment-resistant posttraumatic stress disorder: the first randomized controlled pilot study", Journal of Psychopharmacology (2011); 25(4): 439-452. doi: 10.1177/0269881110378371. Epub Jul. 19, 2010.
Mokler D J et al: "The 5HT"2 antagonist pirenperone reverses disruption of FR-40 by hallucinogenic drugs." Pharmacology Biochemistry and Behavior, Elsevier, US, vol. 22, No. 5, May 1, 1985 (May 1, 1985), pp. 677-682, XP023807793, ISSN: 0091-3057, DOI: 10.1016/0091-3057(85)90512-X [retrieved on May 1, 1985].
National Center for Biotechnology Information (2023). PubChem Substance Record for SID 309311543, SID 309311543, Source: Aurora Fine Chemicals LLC. Modified Jan. 30, 2016, retrieved from https://pubchem.ncbi.nlm.nih.gov/substance/309311543, 5 pages.
National Center for Biotechnology Information. PubChem Compound Summary for CID 10624, Psilocybin. https://pubchem.ncbi.nlm.nih.gov/compound/Psilocybin. Create date Mar. 3, 2005, Accessed May 5, 2025. 62 pages.
National Center for Biotechnology Information. PubChem Compound Summary for CID 123606, Almotriptan. https://pubchem.ncbi.nlm.nih.gov/compound/Almotriptan, Aug. 8, 2005, 53 pages.
National Center for Biotechnology Information. PubChem Compound Summary for CID 149771082, 1-[3-[2-(dimethylamino)ethyl]-1H-indol-4-yl]-N-methylmethanesulfonamide. https://pubchem.ncbi.nlm.nih.gov/compound/149771082, Aug. 2020 pp. 1-8.
National Center for Biotechnology Information. PubChem Compound Summary for CID 15274381, 2-(7-Bromo-1H-indol-3-yl)ethan-1-amine. https://pubchem.ncbi.nlm.nih.gov/compound/2-_7-Bromo-1H-indol-3-yl_ethan-1-amine, Create date Feb. 9, 2007, Modify date Jan. 25, 2025, 14 pages.
National Center for Biotechnology Information. PubChem Compound Summary for CID 156821129, [3-[2-(Dimethylamino)ethyl]-4-hydroxyindol-1-yl]methylphosphonic acid. https://pubchem.ncbi.nlm.nih.gov/compound/156821129, created Nov. 20, 2021, Modify date Aug. 23, 2024, 10 pages.
National Center for Biotechnology Information. PubChem Compound Summary for CID 157042555, [2-bromo-3-[2-(dimethylamino)ethyl]-1H-indol-4-yl] acetate. https://pubchem.ncbi.

(56) References Cited

OTHER PUBLICATIONS nlm.nih.gov/compound/157042555. Create date: Nov. 30, 2021, Modify date: Apr. 12, 2025, accessed Apr. 16, 2025, pp. 1-9.
National Center for Biotechnology Information. PubChem Compound Summary for CID 162478135, 3-[2-(dimethylamino)ethyl]-2-fluoro-1H-indol-4-ol. https://pubchem.ncbi.nlm.nih.gov/compound/3-_2-_dimethylamino_ethyl_-2-fluoro-1H-indol-4-ol. Create date: Feb. 6, 2022, Modify date: Apr. 12, 2025, Accessed Apr. 16, 2025, pp. 1-9.
National Center for Biotechnology Information. PubChem Compound Summary for CID 162478146, [3-[2-(dimethylamino)ethyl]-2-fluoro-1H-indol-4-yl] acetate. https://pubchem.ncbi.nlm.nih.gov/compound/162478146, Create date Feb. 6, 2022, Modify date: Mar. 29, 2025, pp. 1-8.
National Center for Biotechnology Information. PubChem Compound Summary for CID 166138444, [3-[2-[di(propan-2-yl)amino]ethyl]-1H-indol-4-yl] dihydrogen phosphate. https://pubchem.ncbi.nlm.nih.gov/compound/166138444, Create date Dec. 20, 2022, pp. 1-7.
National Center for Biotechnology Information. PubChem Compound Summary for CID 24801868, 4-Acetoxy-N,N-diisopropyltryptamine. https://pubchem.ncbi.nlm.nih.gov/compound/4-Acetoxy-N_N-diisopropyltryptamine. Create date: Jun. 6, 2008, Modify date Mar. 29, 2025, accessed Apr. 4, 2025, 21 pages.
National Center for Biotechnology Information. PubChem Compound Summary for CID 24802108, N-Isopropyl-N-(2-(4-methoxy-1H-indol-3-yl)ethyl)propan-2-amine. https://pubchem.ncbi.nlm.nih.gov/compound/24802108. Create: Jun. 6, 2008, Modify: Mar. 29, 2025, Accessed Apr. 5, 2025. 13 pages.
National Center for Biotechnology Information. PubChem Compound Summary for CID 6089, Dimethyltryptamine. https://pubchem.ncbi.nlm.nih.gov/compound/Dimethyltryptamine. Create date: Mar. 26, 2005 (Mar. 26, 2005), 6 pages.
National Center for Biotechnology Information. PubChem Compound Summary for CID 84056101, 2-(2-chloro-4-methoxy-1H-indol-3-yl)ethanamine. https://pubchem.ncbi.nlm.nih.gov/compound/2-_2-chloro-4-methoxy-1H-indol-3-yl_ethanamine, Create date Oct. 20, 2014, 7 pages.
National Center for Biotechnology Information. PubChem Compound Summary for CID 84058691, 1-(2-chloro-4-methoxy-1H-indol-3-yl)propan-2-amine. https://pubchem.ncbi.nlm.nih.gov/compound/1-_2-chloro-4-methoxy-1H-indol-3-yl_propan-2-amine, Oct. 20, 2014, pp. 1-7.
National Center for Biotechnology Information. PubChem Compound Summary for CID 88309097, [1-[[2-(1H-indol-3-yl)-1-(2-methylphenyl)ethyl]amino]-2-oxoethyl]carbamate. https://pubchem.ncbi.nlm.nih.gov/compound/88309097, Created date Feb. 12, 2015, Modified date Nov. 9, 2024, 8 pages.
National Center for Biotechnology Information. PubChem Substance Record for SID 310331158, SID 310331158, Source: Aurora Fine Chemicals LLC. https://pubchem.ncbi.nlm.nih.gov/substance/310331158, Modify Date: Feb. 15, 2015, 4 pages.
National Center for Biotechnology Information. PubChem Substance Record for SID 313512691, 1H-Indole-4-methanol, 3-(2-aminoethyl)-, Source: Chemhere. https://pubchem.ncbi.nlm.nih.gov/substance/313512691, Jun. 11, 2016, 5 pages.
National Center for Biotechnology Information. PubChem Substance Record for SID 369863280, SID 369863280, Source: Ambinter. https://pubchem.ncbi.nlm.nih.gov/substance/369863280. Deposit date May 25, 2018, Modify Date: May 25, 2018, 5 pages.
National Center for Biotechnology Information. PubChem Substance Record for SID 433987242, N,N-dimethyltryptamine, Source: BioCyc. https://pubchem.ncbi.nlm.nih.gov/substance/433987242, Available Date: Sep. 28, 2020 [retrieved on Mar. 2, 2023, 7 pages.
National Center for Biotechnology Information. PubChem Substance Record for SID 471368824, SID 471368824, Source: PatentScope (WIPO). https://pubchem.ncbi.nlm.nih.gov/substance/471368824. Available Date Sep. 27, 2002, 5 pages.
National Center for Biotechnology Information. PubChem Substance Record for SID 474211406, 3-(2-aminoethyl)-1H-indole-4-carboxylic acid, Source: Enamine. https://pubchem.ncbi.nlm.nih.gov/substance/474211406. Available Date Dec. 15, 2002 [retrieved on Feb. 1, 2023], 7 pages.
National Center for Biotechnology Information. PubChem Substance Record for SID 627609, 2-(1H-indol-3-yl)ethanamine, Source: NIAID ChemDB. https://pubchem.ncbi.nlm.nih.gov/substance/627609, Modify Date: Jan. 21, 2015 [retrieved on Mar. 2, 2023]. 8 pages.
Nichols, D. E., "Psychedelics." Pharmacol Rev. Apr. 2016;68(2):264-355.
Nichols, "Hallucinogens." Pharmacol Ther. Feb. 2004; 101(2):131-81.
Nichols, "Structure-Activity Relationships of Phenethylamine Hallucinogens." J Pharm Sci. Aug. 1981; 70(8): 839-49.
Oliver et al., "Beta-blockers: Historical Perspective and Mechanisms of Action." Rev Esp Cardiol (Engl Ed). Oct. 2019; 72(10): 853-862).
Olson, David E., "The Subjective Effects of Psychedelics May Not Be Necessary for Their Enduring Therapeutic Effects", ACS Pharmacol Transl Sci. Apr. 9, 2021; 4(2): 563-567. Published online Dec. 10, 2020.
Ott, J., "Pharmañopo—Psychonautics: Human intranasal, sublingual, intrarectal, pulmonary and oral pharmacology of bufotenine." J Psychoactive Drugs. Jul.-Sep. 2001; 33(3): 273-81.
Ott, J., "Pharmepena-psychonautics: human intranasal, sublingual and oral pharmacology of 5-methoxy-N, N-dimethyl-tryptamine." J Psychoactive Drugs. Oct.-Dec. 2001;33(4):403-7.
Pandy-Szekeres et al., "GPCRdb in 2023: state-specific structure models using AlphaFold2 and new ligand resources", Nucleic Acids Res. Jan. 6, 2023; 51(D1): D395-D402. 8 pages.
Pandy-Szekeres et al., "The G Protein Database, GproteinDb." Nucleic Acids Res. Jan. 7, 2022; 50(D1): D518-D525.
Perez Custodio et al., "25B-NBOMe, a novel N-2-methoxybenzyl-phenethylamine (NBOMe) derivative, may induce rewarding and reinforcing effects via a dopaminergic mechanism: evidence of abuse potential." Addict Biol. Nov. 2020; 25(6):e12850. doi: 10.1111/adb.12850. Epub Nov. 20, 2019, 12 pages.
Pokorny et al., "Modulatory effect of the 5-HT1A agonist buspirone and the mixed non-hallucinogenic 5-HT1A/2A agonist ergotamine on psilocybin-induced psychedelic experience." Eur Neuropsychopharmacol. Apr. 2016; 26(4):756-66. doi: 10.1016/j.euroneuro.2016.01.005. Epub Jan. 22, 2016.
Pottie et al., "Identification of psychedelic new psychoactive substances (NPS) showing biased agonism at the 5-HT2AR through simultaneous use of β-arrestin 2 and miniGαq bioassays", Biochem Pharmacol. Dec. 2020: 182: 114251. Epub Sep. 28, 2020. 37 pages.
Preller et al., "Effects of serotonin 2A/1A receptor stimulation on social exclusion processing," PNAS, May 3, 2016, vol. 113, No. 18, 5119-5124.
Preller et al., "Role of the 5-HT2A Receptor in Self- and Other-Initiated Social Interaction in Lysergic Acid Diethylamide-Induced States: A Pharmacological fMRI Study", Journal of Neuroscience (Apr. 2018); 38(14): 3603-3611. doi: 10.1523/JNEUROSCI.1939-17.2018. Epub Mar. 19, 2018.
Preller et al., "The fabric of meaning and subjective effects in LSD-induced states depend on serotonin 2A receptor activation", Current Biology (2017); 27(3): 451-457. doi: 10.1016/j.cub.2016.12.030. Epub Jan. 26, 2017.
Prescribing information for Brevibloc (Esmolol Hydrochloride): www.baxterpi.com/pi-pdf/Brevibloc_PI.pdf), Initial U.S. approval: 1986, revised Apr. 2018, 19 pages.
Puledda et al., "An update on migraine: current understanding and future directions," J Neurol (2017) 264:2031-2039.
Puri et al., "Thiolation of Biopolymers for Developing Drug Delivery Systems with Enhanced Mechanical and Mucoadhesive Properties: A Review." Polymers (Basel). Aug. 11, 2020;12(8): 1803. doi: 10.3390/polym12081803. 27 pages.
Ray, T., "Psychedelics and the Human Receptorome," PLoS ONE (2010) 5(2): e9019, 17 pages.
Riba, et al., "Metabolism and urinary disposition of N,N-dimethyltryptamine after oral and smoked administration: a comparative study", Drug Test Anal. May 2015;7(5): 401-6. Epub Jul. 28, 2014.

(56) References Cited

OTHER PUBLICATIONS

Roth et al., "High-affinity Agonist Binding Is Not Sufficient for Agonist Efficacy at 5-Hydroxytryptamine2A Receptors: Evidence in Favor of a Modified Ternary Complex Model", The Journal of Pharmacology and Experimental Therapeautics, 1997, vol. 280, No. 2, pp. 576-583.
Ruiz et al., "Routes of Drug Administration: Dosage, Design, and Pharmacotherapy Success", In book: ADME Processes in Pharmaceutical Sciences, Chapter 6, Jan. 2018, DOI:10.1007/978-3-319-99593-9_6, 44 pages.
Santos-Longhurst, A, "How Long Does DMT Last?" Healthline.com, Nov. 24, 2019, [online] retrieved on Jun. 24, 2022 from https://www.healthline.com/health/how-long-does-dmt-last, 12 pages.
Sargent et al., "Radiohalogen-Labeled Imaging Agents. 3. Compounds for Measurement of Brain Blood Flow by Emission Tomography," Journal of Medicinal Chemistry (1984), 27(8), 1071-1077.
Schifano et al., "New psychoactive substances (NPS) and serotonin syndrome onset: A systematic review", Exp Neurol. May 2021: 339: 113638. Epub Feb. 8, 2021. 29 pages.
Schindler et al., "Exploratory Controlled Study of the Migraine-Suppressing Effects of Psilocybin", Neurotherapeutics, Jan. 2021; 18(1): 534-543. Epub Nov. 12, 2020. 10 pages.
Schlag et al., "Adverse effects of psychedelics: From anecdotes and misinformation to systematic science." J Psychopharmacol. Mar. 2022; 36(3): 258-272.
Shen et al., "Psychedelic 5-Methoxy-N,N-dimethyltryptamine: Metabolism, Pharmacokinetics, Drug Interactions, and Pharmacological Actions", Curr Drug Metab., Oct. 2010; 11(8): 659-666.
Shen L, et al., "Bufotenines-loaded liposome exerts anti-inflammatory, analgesic effects and reduce gastrointestinal toxicity through altering lipid and bufotenines metabolism", Biomed Pharmacother, Sep. 2022, vol. 153, pp. 1-12.
Sherwood et al., "Synthesis and characterization of 5-MeO-DMT succinate for clinical use", ACS Omega (2020); 5(49): 32067-32075. doi: 10.1021/acsomega.0c05099.
Sigma, Succinic acid—Butanedioic acid, CAS No. 110-15-6, Merck KGaA, 2023, 4 pages.
Sizemore et al., "Serotonergic Modulation Across Sensory Modalities." J Neurophysiol. Jun. 1, 2020;123(6):2406-2425. doi: 10.1152/jn.00034.2020. Epub May 13, 2020.
Sizemore, T.R, and Dacks, A.M., "Circadian Clocks: Mosquitoes Master the Dark Side of the Room", Curr Biol. Aug. 17, 2020; 30(16): R932-R934. 3 pages.
Strassman, "Dose-response study of N,N-dimethyltryptamine in humans. I. Neuroendocrine, autonomic, and cardiovascular effects", Arch Gen Psychiatry. Feb. 1994; 51(2): 85-97.
Strassman, "N-dimethyltryptamine in humans: II. Subjective effects and preliminary results of a new rating scale", Arch Gen Psychiatry. Feb. 1994; 51(2): 98-108.
Terry, Alvin V., "Drugs that target serotonergic receptors." Cognitive Enhancing Drugs, pp. 79-80, Ed. J. Buccafusco, Birkhauser, 2004, 2 pages.
Thoai, et al., "Design and Synthesis of Sustain-Acting Melatonin Prodrugs", Sep. 12, 2013 (Sep. 12, 2013), Journal of Chemistry, vol. 2013, Issue 1, pp. 1-6.
Timmermann, Christopher et al. "Neural correlates of the DMT experience assessed with multivariate EEG." Sci Rep. Nov. 19, 2019;9(1):16324. 13 pages.
Tirapegui et al., "Synthesis of N-(halogenated) benzyl analogs of superpotent serotonin ligands," J. Chil. Chem. Soc., (2014) 59, No. 3, pp. 2625-2627.
Titeler et al., "Radioligand binding evidence implicates the brain 5 HT2 receptor as a site of action for LSD and phenylisopropylamine hallucinogens", Psychopharmacology (Berl). (1988); 94: 213-216. doi: 10.1007/BF00176847.
Tomaszewski et al., "Benzofuran Bioisosteres of Hallucinogenic Tryptamines," J. Med. Chem., 1992, 35, pp. 2061-2064.
University of Zurich. Compositions and kits comprising N,N-dimethyltryptamine and harmine and their use in therapy. European Patent Application Serial No. EP20181489, filing date Jun. 24, 2020, receipt by WIPO Jul. 6, 2021. 56 pages.
U.S. Appl. No. 19/173,537, filed Apr. 8, 2025, by Witowski et al.
U.S. Appl. No. 19/258,381, filed Jul. 2, 2025, by Fawaz et al.
Uthaug et al., "A single inhalation of vapor from dried toad secretion containing 5-methoxy-N,N-dimethyltryptamine (5-MeO-DMT) in a naturalistic setting is related to sustained enhancement of satisfaction with life, mindfulness-related capacities, and a decrement of psychopathological symptoms," Psychopharmacology (2019) 236:2653-2666.
Uthaug et al., "Prospective examination of synthetic 5-methoxy-N,N-dimethyltryptamine inhalation: effects on salivary IL-6, cortisol levels, affect, and non-judgment," Psychopharmacology (2020) 237:773-785.
Valle et al., "Inhibition of alpha oscillations through serotonin-2A receptor activation underlies the visual effects of ayahuasca in humans", European Neuropsychopharmacology (2016); 26(7): 1161-1175. doi: 10.1016/j.euroneuro.2016.03.012. Epub Mar. 25, 2016.
Viracocha, "The DMT Handbook." Dec. 2008, URL:https://catbull.com/alamut/Bibliothek/DMT_Handbook.pdf. 31 pages.
Vollenweider et al., "Psilocybin induces schizophrenia-like psychosis in humans via a serotonin-2 agonist action", Neuroreport (1998); 9(17): 3897-3902. doi: 10.1097/00001756-199812010-00024.
Vollenweider et al., "Psychedelic drugs: neurobiology and potential for treatment of psychiatric disorders", Nature Reviews Neuroscience (2020); 21(11): 611-624. doi: 10.1038/s41583-020-0367-2. Epub Sep. 14, 2020.
Wang et al., "Anti-inflammatory and analgesic actions of bufotenine through inhibiting lipid metabolism pathway," Biomedicine & Pharmacotherapy (2021) 140: 111749, 11 pages.
Wey et al., "Structure-based design, synthesis, and biological evaluation of indomethacin derivatives as cyclooxygenase-2 inhibiting nitric oxide donors." J Med Chem. Dec. 13, 2007;50(25):6367-82. doi: 10.1021/jm0611861. Epub Nov. 10, 2007.
Wikipedia, "Perfusion", Dec. 29, 2020 (Dec. 29, 2020), retrieved on Jun. 24, 2022 from https://en.wikipedia.org/w/index.php?title=Perfusion&oldid=996968059; 5 pages.
Winter et al., "Psilocybin-induced stimulus control in the rat", Pharmacology Biochemistry and Behavior (2007); 87(4): 472-480. doi: 10.1016/j.pbb.2007.06.003. Epub Jun. 22, 2007.
Winter et al., "The Paradox of 5-Methoxy-N,N-Dimethyltryptamine: An Indoleamine Hallucinogen That Induces Stimulus Control via 5-HT1A Receptors," Pharmacology Biochemistry and Behavior, 2000, vol. 65, No. 1, pp. 75-82.
Wolff, M., "Burger's Medicinal Chemistry and Drug Discovery", Fifth Edition, John Wiley & Sons (1995); 1: 975-977.
Wood et al., "Prevalence of use and acute toxicity associated with the use of NBOMe drugs", Clin Toxicol (Phila). Feb. 2015; 53(2): 85-92. doi:10.3109/15563650.2015.1004179.
Yu, A.M., "Indolealkylamines: Biotransformations and Potential Drug-Drug Interactions," The AAPS Journal, Jun. 2008, vol. 10, No. 2, pp. 242-253.
Zamberlan et al., "The Varieties of the Psychedelic Experience: A Preliminary Study of the Association Between the Reported Subjective Effects and the Binding Affinity Profiles of Substituted Phenethylamines and Tryptamines", Front Integr Neurosci. Nov. 8, 2018: 12: 54. eCollection 2018. 22 pages.

* cited by examiner

CRYSTALLINE FORMS OF N,N-DIMETHYLTRYPTAMINE AND METHODS OF USING THE SAME

CROSS-REFERENCE TO RELATED APPLICATION

This application claims priority to U.S. Provisional Application No. 63/429,369, titled "CRYSTALLINE FORMS OF N,N-DIMETHYLTRYPTAMINE AND METHODS OF USING THE SAME" and filed Dec. 1, 2022, the content of which is incorporated herein by reference in its entirety.

BACKGROUND OF THE INVENTION

N,N-dimethyltryptamine (N,N-DMT) has therapeutic value as a psychedelic, with intrinsic properties making it an attractive possible medication, especially for neurological diseases and conditions. Crystalline forms of active pharmaceutical ingredients offer the best means for controlling important physiochemical qualities, such as stability, solubility, bioavailability, particle size, bulk density, flow properties, polymorphic content, and other properties. Two crystalline forms of N,N-DMT have been previously identified and designated as "Form I" (Bergin et al. *Acta Crystallogr.* , Sect. B24, 882 (1968) and Gaujac et al. *Talanta* 106, 394 (2013)) and "Form II" (Falkenberg et al. *Acta Crystallogr.*, Sect B28, 3075 (1972)). There remains a need in the art to develop additional crystalline forms of N,N-DMT.

BRIEF SUMMARY OF THE INVENTION

The present disclosure relates to crystalline forms of N,N-dimethyltryptamine

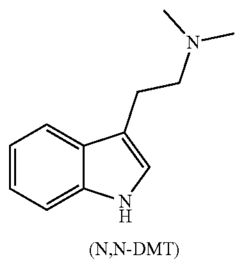

(N,N-DMT)

In embodiments, the present disclosure provides Form IV of N,N-dimethyltryptamine.

In embodiments, Form IV is characterized by peaks in an X-ray powder diffraction (XRPD) pattern at 13.6±0.2, 20.8±0.2, and 17.8±0.2°2θ. In embodiments, Form IV is further characterized by at least one XRPD peak selected from 13.9±0.2, 14.0±0.2, 15.4±0.2, 18.6±0.2, 23.6±0.2, 24.5±0.2, 26.0±0.2, or 26.7±0.2°2θ.

In embodiments, Form IV is characterized by peaks in an XRPD pattern at 13.6±0.2, 17.8±0.2, and 20.8±0.2 and at least one XRPD peak selected from 13.9±0.2, 14.0±0.2, 15.4±0.2, 18.6±0.2, 23.6±0.2, 24.5±0.2, 26.0±0.2, or 26.7=0.2°2θ.

In embodiments, Form IV is characterized by peaks in an XRPD pattern at 13.6±0.2, 13.9±0.2, 14.0±0.2, 15.4±0.2, 17.8±0.2, 18.6±0.2, 20.8±0.2, 23.6±0.2, 24.5±0.2, 26.0±0.2, and 26.7±0.2°2θ.

In embodiments, Form IV is characterized by peaks in an XRPD pattern at 7.7±0.2, 10.4±0.2, 11.9±0.2, 13.0±0.2, 13.6±0.2, 13.9±0.2, 14.0±0.2, 15.2±0.2, 15.4±0.2, 16.2±0.2, 16.9±0.2, 17.5±0.2, 17.8±0.2, 18.1±0.2, 18.6±0.2, 19.3±0.2, 19.8±0.2, 20.8±0.2, 21.1±0.2, 21.6±0.2, 22.4±0.2, 22.7±0.2, 23.6±0.2, 23.8±0.2, 24.5±0.2, 24.8±0.2, 25.2±0.2, 26.1±0.2, 26.7±0.2, 26.9±0.2, 27.5±0.2, 28.0±0.2, 28.2±0.2, 28.6±0.2, 28.8±0.2, 29.3±0.2, 29.5±0.2, 29.6±0.2, 30.2±0.2, 30.4±0.2, 30.6±0.2, 30.9±0.2, 31.1±0.2, 31.6±0.2, 31.9±0.2, 32.8±0.2, 33.2±0.2, 33.7±0.2, 34.5±0.2, and 35.3±0.2°2θ.

In embodiments, Form IV is characterized an XRPD pattern substantially similar to that shown in FIG. 3.

In embodiments, Form IV exhibits a Differential Scanning Calorimetry (DSC) thermogram comprising an endotherm peak with an onset at 69±5° C. In embodiments, Form IV exhibits a DSC thermogram comprising an endothermic peak at 70±5° C.

In embodiments, Form IV exhibits substantially no weight loss at a temperature under 225±5° C. as measured by thermogravimetric (TGA) analysis.

In embodiments, Form IV exhibits a melting point of 69±5° C.

In embodiments, the present disclosure provides Form III of N,N-dimethyltryptamine.

In embodiments, Form III is characterized by peaks in an XRPD pattern at 7.6±0.2 and 15.2±0.2 In embodiments, Form III is further characterized by at least one XRPD peak selected from 19.2±0.2° 2θ, 19.6±0.2 or 23.0=0.2°2θ.

In embodiments, Form III is characterized by peaks in an XRPD pattern at 7.6±0.2, 15.2±0.2, 19.2±0.2, 19.6±0.2, and 22.9±0.2°2θ.

In embodiments, Form III is characterized by peaks in an XRPD pattern at 7.6±0.2, 15.2±0.2, 16.8±0.2, 19.2±0.2, 19.6±0.2, 20.0±0.2, 20.4±0.2, 20.7±0.2, 21.5±0.2, 22.4±0.2, 22.9±0.2, 23.1±0.2, 26.3±0.2, 27.1±0.2, 27.8±0.2, 28.5±0.2, 30.7±0.2, and 31.56=0.2°2θ.

In embodiments, Form III is characterized an XRPD pattern substantially similar to that shown in FIG. 2.

In embodiments, Form III exhibits a DSC thermogram comprising an endotherm peak with an onset at 67±5° C. In embodiments, Form III exhibits a DSC thermogram comprising an endothermic peak at 68±5° C.

In embodiments, Form III exhibits substantially no weight loss at a temperature under 200±5° C. as measured by TGA analysis.

In embodiments, Form III exhibits a melting point of 39±5° C.

In embodiments, the present disclosure provides pharmaceutical compositions comprising Form IV of N,N-dimethyltryptamine. In embodiments, the pharmaceutical composition further comprises a pharmaceutically acceptable excipient. In embodiments, the present disclosure provides an oral dosage form comprising Form IV of N,N-dimethyltryptamine.

In embodiments, the present disclosure provides pharmaceutical compositions comprising Form III of N,N-dimethyltryptamine. In embodiments, the pharmaceutical composition further comprises a pharmaceutically acceptable excipient. In embodiments, the present disclosure provides an oral dosage form comprising Form III of N,N-dimethyltryptamine.

The present disclosure provide methods of treating post-traumatic stress disorder (PTSD) in a subject in need thereof, comprising administering a therapeutically effective amount of a Form IV of N,N-dimethyltryptamine, Form III of N,N-dimethyltryptamine, a pharmaceutical composition, or an oral dosage form described herein to the subject.

The present disclosure provide methods of treating post-traumatic stress disorder (PTSD) in a subject in need thereof, comprising administering a therapeutically effective amount of a Form IV of N,N-dimethyltryptamine, Form III of N,N-dimethyltryptamine, a pharmaceutical composition, or an oral dosage form described herein to the subject. In embodiments, the depression is a major depressive disorder (MDD) or treatment-resistant depression (TRD).

The present disclosure provide methods of treating an anxiety disorder in a subject in need thereof, comprising administering a therapeutically effective amount of a Form IV of N,N-dimethyltryptamine, Form III of N,N-dimethyltryptamine, a pharmaceutical composition, or an oral dosage form to the subject.

DETAILED DESCRIPTION OF THE INVENTION

Figure 1:
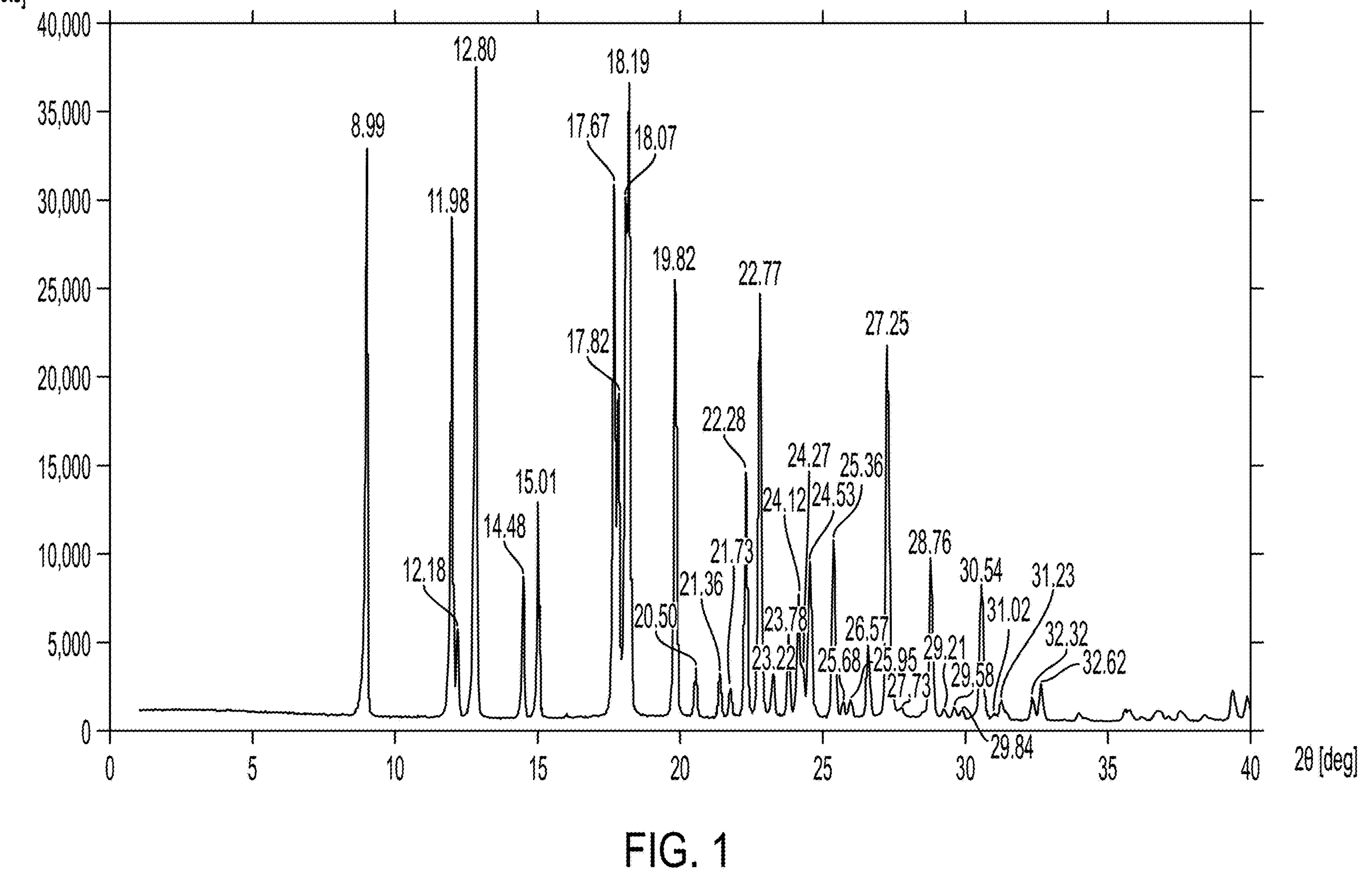
FIG. 1 shows the XRPD diffractogram of a sample of Form I of N,N-DMT.

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

The terms "administer," "administering" or "administration" as used herein refer to administering a compound or pharmaceutically acceptable salt of the compound or a composition or formulation comprising the compound or pharmaceutically acceptable salt of the compound to a patient.

The term "preventing" as used herein with regard to a patient or subject, refers to preventing the onset of disease development if none had occurred, preventing the disease or disorder from occurring in a subject or a patient that may be predisposed to the disorder or disease but has not yet been diagnosed as having the disorder or disease, and/or preventing further disease/disorder development if already present.

The term "substantially similar" as used herein with regards to an analytical spectrum, such as an XRPD pattern, means that a spectrum resembles the reference spectrum in both the peak locations and their relative intensities, allowing for variability appropriate in the art. For example, two spectra may be regarded as "substantially similar" when the two spectra share defining characteristics sufficient to differentiate them from a spectrum obtained for a different solid form. In embodiments, spectra or characterization data that are substantially similar to those of a reference crystalline form are understood by those of ordinary skill in the art to correspond to the same crystalline form as the particular reference. In analyzing whether spectra or characterization data are substantially similar, a person of ordinary skill in the art understands that particular characterization data points may vary to a reasonable extent while still describing a given solid form, due to, for example, experimental error and routine sample-to-sample analysis.

The term "treating" as used herein with regard to a patient or subject, refers to improving at least one symptom of the patient's or subject's disorder. In some embodiments, treating can be improving, or at least partially ameliorating a disorder or one or more symptoms of a disorder.

The term "therapeutically effective" applied to dose or amount refers to that quantity of a compound or pharmaceutical formulation that is sufficient to result in a desired clinical benefit after administration to a patient or subject in need thereof.

All XRPD peaks and patterns are given in °2θ using Cu Kα1 radiation at a wavelength of 1.5406 Å. The values of degree 2θ allow appropriate error margins. For example, the degree 2θ of about "17.48±0.2" denotes a range from about 17.46 to 17.50 degree 2θ. Depending on the sample preparation techniques, the calibration techniques applied to the instruments, human operational variation, and etc., those skilled in the art recognize that the appropriate error of margins for a XRPD can be ±0.2, which includes any value below ±0.2 such as ±0.1; ±0.05; or less.

TGA and DSC thermograms for a given crystalline form of the same compound will vary within a margin of error. The values of a single peak, expressed in degree Celsius, allow appropriate error margins. Typically, the error margins are represented by "±". For example, the single peak characteristic value of about "120±5" denotes a range from about 115 to 125. Depending on the sample preparation techniques, the calibration techniques applied to the instruments, human operational variations, and etc., those skilled in the art recognize that the appropriate error of margins for a single peak characteristic value can be ±5, which includes any value below ±5 such as ±4, ±3.5, ±3, ±2.5; ±2.0; ±1.5; ±1.0; ±0.5; or less.

The following description includes information that may be useful in understanding the present invention. It is not an admission that any of the information provided herein is prior art or relevant to the presently claimed inventions, or that any publication specifically or implicitly referenced is prior art.

Crystalline Forms of N,N-dimethyltryptamine (N,N-DMT)

In one aspect, the present disclosure provides crystalline forms of N,N-DMT. In embodiments, the crystalline form of N,N-DMT is Form III. In embodiments, the crystalline form of N,N-DMT is Form IV. In embodiments, the crystalline form of N,N-DMT is a mixture of Form III and Form IV.

In embodiments, the crystalline form of N,N-DMT comprises a mixture of one or more forms of N,N-DMT (e.g., Form III or IV). In some embodiments, the crystalline form of N,N-DMT comprises a substantially pure form of one form of N,N-DMT. In embodiments, the substantially pure form is Form III. In embodiments, the substantially pure form is Form IV.

In embodiments, the crystalline form of N,N-DMT comprises greater than about 99.9%, about 99.8%, about 99.7%, about 99.6%, about 99.5%, about 99.4%, about 99.3%, about 99.2%, about 99.1%, or about 99.0% of one form of N,N-DMT (e.g., Form III and/or Form IV).

In embodiments, the crystalline form of N,N-DMT comprises greater than about 99%, 98%, 97%, 96%, 95%, 94%, 93%, 92%, 91%, or 90% of one form of N,N-DMT. In some embodiments, the crystalline form of N,N-DMT comprises greater than about 90%, 85%, 80%, 75%, 70%, 65%, 60%, 55%, 50%, 45%, or 40% of one form of N,N-DMT (e.g., Form III and/or Form IV).

I. Form III

In embodiments, the crystalline form of N,N-DMT is Form III.

In embodiments, Form III is characterized by peaks in a XRPD pattern at 7.6±0.2 and 15.2±0.2. In embodiments, the variance at any of these peaks is ±0.1 °2θ.

In embodiments, Form III is characterized by peaks in a XRPD pattern at 7.6±0.2 and 15.2±0.2 and least one peak in an XRPD pattern selected from 19.2±0.2°2θ, 19.6±0.2 or 23.0±0.2 °2θ. In embodiments, the variance at any of these peaks is ±0.1 °2θ.

In embodiments, Form III is characterized by peaks in a XRPD pattern at 7.6±0.2, 15.2±0.2, 19.2±0.2, and 19.6±0.2°2θ. In embodiments, the variance at any of these peaks is ±0.1 °2θ.

In embodiments, Form III is characterized by peaks in a XRPD pattern at 7.6±0.2, 15.2±0.2, 19.2±0.2, and 23.0±0.2°2θ. In embodiments, the variance at any of these peaks is ±0.1 °2θ.

In embodiments, Form III is characterized by peaks in an XRPD pattern at 7.6±0.2, 15.2±0.2, 19.2±0.2, 19.6±0.2, and 22.9±0.2°2θ. In embodiments, the variance at any of these peaks is ±0.1 °2θ.

In embodiments, Form III is characterized by peaks in an XRPD pattern at 7.6±0.2, 15.2±0.2, 16.8±0.2, 19.2±0.2, 19.6±0.2, 20.0±0.2, 20.4±0.2, 20.7±0.2, 21.5±0.2, 22.4±0.2, 22.9±0.2, 23.1±0.2, 26.3±0.2, 27.1±0.2, 27.8±0.2, 28.5±0.2, 30.7±0.2, and 31.56=0.2°2θ.

Figure 2:
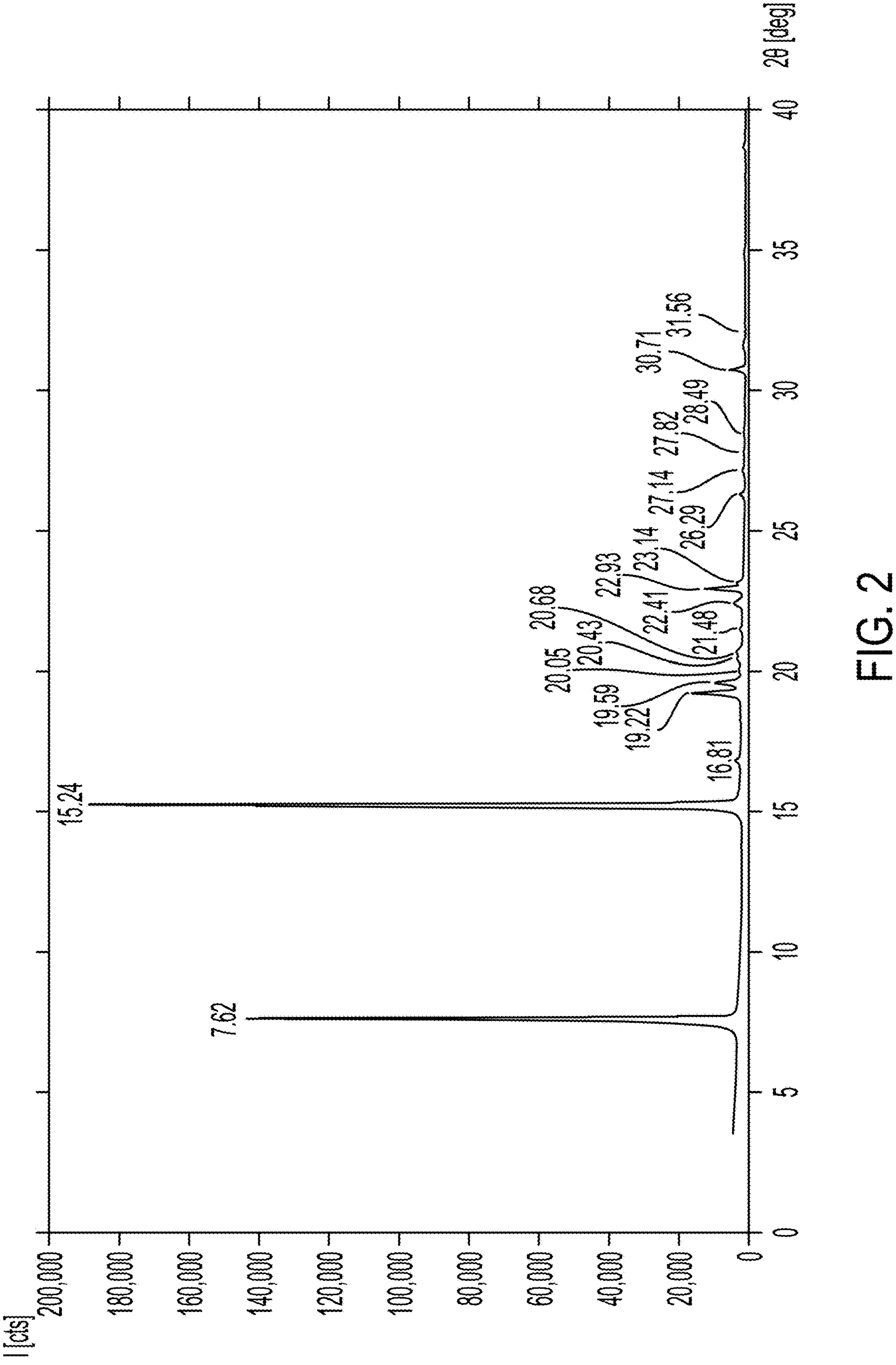
FIG. 2 shows the XRPD diffractogram of a sample of Form III of N,N-DMT.

In embodiments, Form III is characterized by an XRPD pattern substantially similar to that shown in FIG. 2.

In embodiments, Form III is characterized by an XRPD pattern comprising peaks show in Table 4.

In embodiments, Form III is characterized by an XRPD pattern comprising peaks show in Table 5.

In embodiments, Form III exhibits a DSC thermogram comprising an endotherm peak with an onset at 67±5° C. In embodiments, Form III exhibits a DSC thermogram comprising an endothermic peak at 68±5° C.

In embodiments, Form III exhibits substantially no weight loss at a temperature under 200±5° C. as measured by TGA analysis.

In embodiments, Form III exhibits a melting point of 39±5° C.

II. Form IV

In embodiments, the crystalline form of N,N-DMT is Form IV.

In embodiments, Form IV is characterized by peaks in a XRPD pattern at 13.6±0.2, 20.8±0.2, and 17.8±0.2° 2θ. In embodiments, the variance at any of these peaks is ±0.1° 2θ.

In embodiments, Form IV is characterized by peaks in a XRPD pattern at 13.6±0.2, 20.8±0.2, and 17.8±0.2°2θ and least one peak in an XRPD pattern selected from 13.9±0.2, 14.0±0.2, 15.4±0.2, 18.6±0.2, 23.6±0.2, 24.5±0.2, 26.0±0.2, or 26.7±0.2° 2θ. In embodiments, the variance at any of these peaks is ±0.1 °2θ.

In embodiments, Form IV is characterized by peaks in a XRPD pattern at 13.6±0.2, 13.9±0.2, 17.8±0.2, and 20.8±0.2°2θ. In embodiments, the variance at any of these peaks is ±0.1 °2θ.

In embodiments, Form IV is characterized by peaks in a XRPD pattern at 13.6±0.2, 15.4±0.2, 17.8±0.2, and 20.8±0.2°2θ. In embodiments, the variance at any of these peaks is ±0.1 °2θ.

In embodiments, Form IV is characterized by peaks in a XRPD pattern at 13.6±0.2, 17.8±0.2, 18.6±0.2, and 20.8±0.2°2θ. In embodiments, the variance at any of these peaks is ±0.1 °2θ.

In embodiments, Form IV is characterized by peaks in a XRPD pattern at 13.6±0.2, 17.8±0.2, 20.8±0.2, and 23.6±0.2°2θ. In embodiments, the variance at any of these peaks is ±0.1 °2θ.

In embodiments, Form IV is characterized by peaks in a XRPD pattern at 13.6±0.2, 17.8±0.2, 20.8±0.2, and 24.5±0.2°2θ. In embodiments, the variance at any of these peaks is ±0.1 °2θ.

In embodiments, Form IV is characterized by peaks in a XRPD pattern at 13.6±0.2, 17.8±0.2, 20.8±0.2, and 26.0±0.2°2θ. In embodiments, the variance at any of these peaks is ±0.1 °2θ.

In embodiments, Form IV is characterized by peaks in a XRPD pattern at 13.6±0.2, 17.8±0.2, 20.8±0.2, and 26.7±0.2°2θ. In embodiments, the variance at any of these peaks is ±0.1 °2θ.

In embodiments, Form IV is characterized by peaks in a XRPD pattern at 13.6±0.2, 20.8±0.2, and 17.8±0.2, and at least one XRPD peak selected from 13.9±0.2, 14.0±0.2, 15.4±0.2, 18.6±0.2, 23.6±0.2, 24.5±0.2, 26.0±0.2, or 26.7±0.2°2θ. In embodiments, the variance at any of these peaks is ±0.1 °2θ.

In embodiments, Form IV is characterized by peaks in a XRPD pattern at 13.6±0.2, 13.9±0.2, 14.0±0.2, 15.4±0.2, 17.8±0.2, 18.6±0.2, 20.8±0.2, 23.6±0.2, 24.5±0.2, 26.0±0.2, and 26.7±0.2°2θ. In embodiments, the variance at any of these peaks is ±0.1 °2θ.

In embodiments, Form IV is characterized by peaks in an XRPD pattern at 7.7±0.2, 10.4±0.2, 11.9±0.2, 13.0±0.2, 13.6±0.2, 13.9±0.2, 14.0±0.2, 15.2±0.2, 15.4±0.2, 16.2±0.2, 16.9±0.2, 17.5±0.2, 17.8±0.2, 18.0±0.2, 18.6±0.2, 19.3±0.2, 19.8±0.2, 20.8±0.2, 21.1±0.2, 21.6±0.2, 22.4±0.2, 22.7±0.2, 23.6±0.2, 23.8±0.2, 24.5±0.2, 24.8±0.2, 25.2±0.2, 26.1±0.2, 26.7±0.2, 26.9±0.2, 27.5±0.2, 28.0±0.2, 28.2±0.2, 28.6±0.2, 28.8±0.2, 29.3±0.2, 29.5±0.2, 29.6±0.2, 30.2±0.2, 30.4±0.2, 30.6±0.2, 30.9±0.2, 31.1±0.2, 31.6±0.2, 31.9±0.2, 32.8±0.2, 33.2±0.2, 33.7±0.2, 34.5±0.2, and 35.3±0.2°2θ. In embodiments, the variance at any of these peaks is ±0.1 °2θ.

Figure 3:
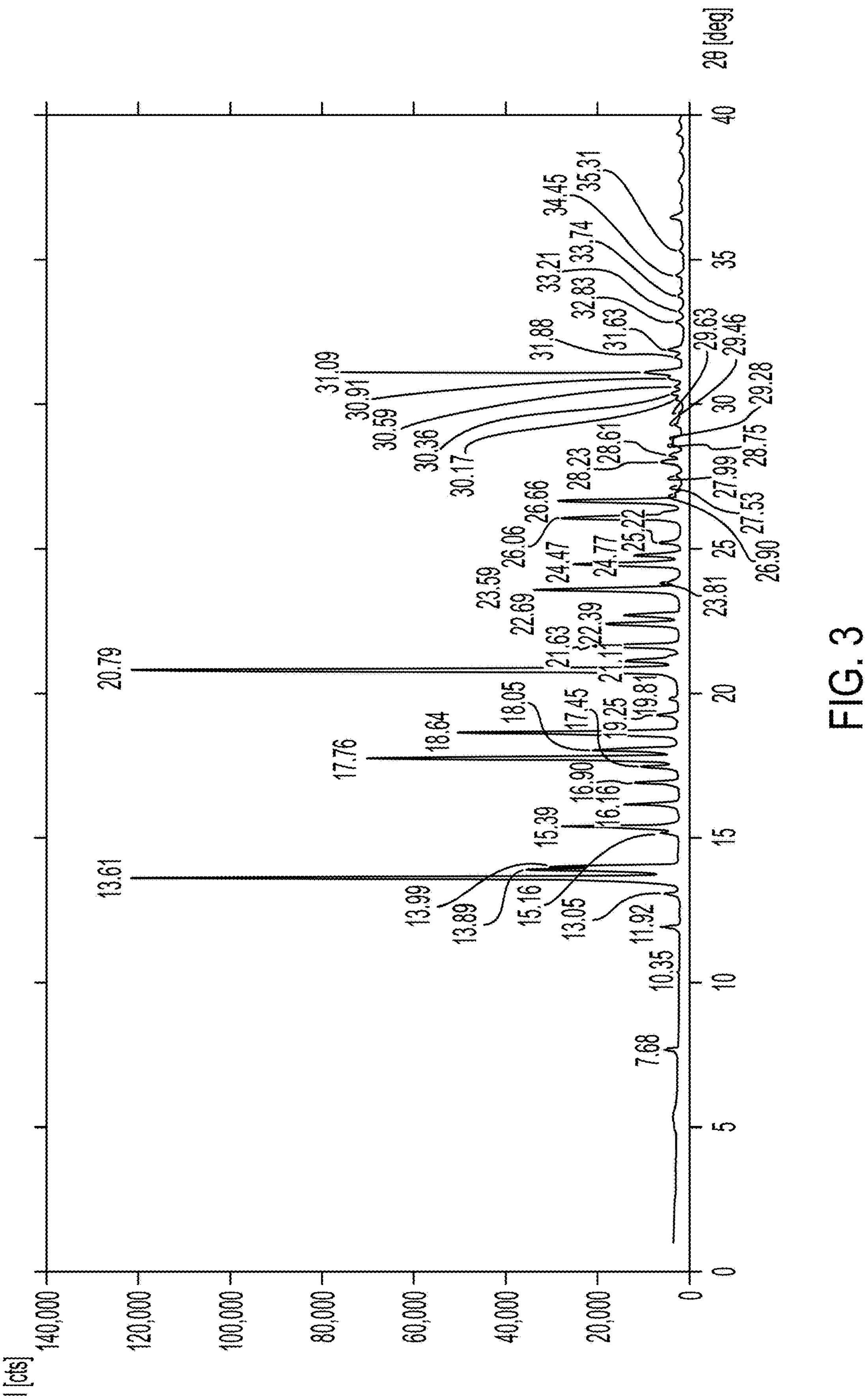
FIG. 3 shows the XRPD diffractogram of a sample of Form IV of N, N-DMT.

In embodiments, Form IV is characterized an XRPD pattern substantially similar to that shown in FIG. 3.

In embodiments, Form IV is characterized by an XRPD pattern comprising peaks show in Table 6.

In embodiments, Form IV is characterized by an XRPD pattern comprising peaks show in Table 7.

In embodiments, Form IV exhibits a DSC thermogram comprising an endotherm peak with an onset at 69±5° C. In embodiments, Form IV exhibits a DSC thermogram comprising an endothermic peak at 70±5° C.

In embodiments, Form IV exhibits substantially no weight loss at a temperature under 225±5° C. as measured by TGA analysis.

In embodiments, Form IV exhibits a melting point of 69±5° C.

Pharmaceutical Compositions

In one aspect, the present disclosure provides compositions comprising a at least one crystalline form of N,N-DMT described herein (e.g., Form III and/or Form IV) and one or more excipients. In embodiments, the composition is a pharmaceutical composition comprising a crystalline form of N,N-DMT, and one or more pharmaceutically acceptable excipients.

In embodiments, the pharmaceutical composition comprises Form III of N,N-DMT.

In embodiments, the pharmaceutical composition comprises Form IV of N,N-DMT.

In embodiments, the composition comprises a pharmaceutically acceptable carrier. In embodiments, a pharmaceutically acceptable carrier includes a pharmaceutically acceptable excipient, binder, adjuvant, and/or diluent. In embodiments, suitable pharmaceutically acceptable carriers include, but are not limited to, inert solid fillers or diluents and sterile aqueous or organic solutions. In embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* $21^{th}$ Edition (Lippincott Williams & Wilkins, 2005).

In embodiments, one or more crystalline forms of N,N-DMT (e.g., Form III and/or Form IV) of the present disclosure are formulated for administration by a variety of means including orally, parenterally, by inhalation spray, topically, or rectally in formulations containing pharmaceutically acceptable carriers, adjuvants, vehicles, or mixtures thereof. The term parenteral as used here includes subcutaneous, intravenous, intramuscular, and intraarterial injections with a variety of infusion techniques. Intraarterial and intravenous injection as used herein includes administration through catheters.

In embodiments, the present disclosure provides oral dosage forms comprising a composition described herein.

In embodiments, the oral dosage form is a solid dosage form such as a tablet, capsule, pill, powder, or granule. Types of oral tablets include compressed, chewable lozenges and tablets, which can be enteric-coated, sugar-coated or film-coated. Capsules can be hard or soft gelatin capsules, while granules and powders can be provided in non-effervescent or effervescent form with the combination of other ingredients known to those skilled in the art.

Therapeutic Methods

In one aspect, the present disclosure provides methods of treating or preventing neurological disorders in a subject in need thereof, the methods comprising administering a therapeutically effective amount of a crystalline form of N,N-DMT disclosed herein (e.g., Form III and/or Form IV) or a pharmaceutical composition thereof to the subject.

In embodiments, the neurological disorder is a mood disorder. In embodiments, the mood disorder is clinical depression, postnatal depression or postpartum depression, perinatal depression, atypical depression, melancholic depression, psychotic major depression, cationic depression, seasonal affective disorder, dysthymia, double depression, depressive personality disorder, recurrent brief depression, major depressive disorder, minor depressive disorder, bipolar disorder or manic depressive disorder, depression caused by chronic medical conditions, treatment-resistant depression, refractory depression, suicidality, suicidal ideation, or suicidal behavior. In embodiments, the method described herein provides therapeutic effect to a subject suffering from depression (e.g., moderate or severe depression). In embodiments, the mood disorder is associated with neuroendocrine diseases and disorders, neurodegenerative diseases and disorders (e.g., epilepsy), movement disorders, tremor (e.g., Parkinson's Disease), or women's health disorders or conditions. In embodiments, the mood disorder is depression. In embodiments, the mood disorder is treatment-resistant depression or major depressive disorder. In embodiments, the mood disorder is major depressive disorder. In embodiments, the mood disorder is treatment-resistant depression.

In embodiments, the present disclosure provides methods of treating or preventing PTSD, mood disorders, general anxiety disorder, addictive disorders, and/or drug dependence in a subject in need thereof, the methods comprising administering a therapeutically effective amount of a crystalline form of N,N-DMT disclosed herein (e.g., Form III and/or Form IV) or a pharmaceutical composition thereof to the subject.

In embodiments, the present disclosure provides methods of treating or preventing PTSD in a subject in need thereof, the methods comprising administering a therapeutically effective amount of a crystalline form of N,N-DMT disclosed herein (e.g., Form III and/or Form IV) or a pharmaceutical composition thereof to the subject.

In embodiments, the present disclosure provides methods of treating or preventing behavioral or mood disorders in a subject in need thereof, the methods comprising administering a therapeutically effective amount of a crystalline form of N,N-DMT disclosed herein (e.g., Form III and/or Form IV) or a pharmaceutical composition thereof to the subject. In embodiments, the behavioral or mood disorder includes anxiety, such as social anxiety in autistic subjects (e.g., autistic adults) and anxiety related to life-threatening illnesses. In embodiments, the behavioral or mood disorder includes stress (where moderation thereof is measured, e.g., by effects on amygdala responses). In embodiments, the anxiety disorder is panic disorder, obsessive-compulsive disorder, and/or general anxiety disorder. In embodiments, the subject suffers from a lack of motivation, attention, lack of accuracy in memory recall, speed of response, perseveration, and/or cognitive engagement. Further examples include depression (e.g., MDD or TRD), attention disorders, disorders of executive function and/or cognitive engagement, obsessive compulsive disorder, bipolar disorder, panic disorder, phobia, schizophrenia, psychopathy, antisocial personality disorder and/or neurocognitive disorders.

In embodiments, the present disclosure provides methods for treating or preventing an addictive disorder in a subject in need thereof, the methods comprising administering a therapeutically effective amount of a crystalline form of N,N-DMT disclosed herein (e.g., Form III and/or Form IV) or a pharmaceutical composition thereof to the subject. In embodiments, the addictive disorder is alcohol abuse, substance abuse, smoking, obesity, or mixtures thereof. In embodiments, the disorder is an cating disorder (e.g., anorexia nervosa, bulimia, nervosa, binge eating disorder, etc.) or an auditory disorder.

In embodiments, the present disclosure provides methods for treating or preventing an impulsive disorder in a subject in need thereof, the methods comprising administering a therapeutically effective amount of a crystalline form of N,N-DMT disclosed herein (e.g., Form III and/or Form IV) or a pharmaceutical composition thereof to the subject. In embodiments, the impulsive disorder is attention deficit hyperactivity disorder (ADHD), attention deficit disorder (ADD), Tourette's syndrome, autism, or combinations thereof.

In embodiments, the present disclosure provides methods for treating or preventing a compulsive disorder in a subject in need thereof, the methods comprising administering a therapeutically effective amount of a crystalline form of N,N-DMT disclosed herein (e.g., Form III and/or Form IV) or a pharmaceutical composition thereof to the subject. In embodiments, the compulsive disorder is obsessive compulsive disorder (OCD), gambling, aberrant sexual behavior, or combinations thereof.

In embodiments, the present disclosure provides methods for treating or preventing a personality disorder in a subject in need thereof, the methods comprising administering a therapeutically effective amount of a crystalline form of N,N-DMT disclosed herein (e.g., Form III and/or Form IV) or a pharmaceutical composition thereof to the subject. In embodiments, the personality disorder is conduct disorder, antisocial personality, aggressive behavior, or combinations thereof to the subject.

In embodiments, the present disclosure provides methods of treating or preventing PTSD, social anxiety disorder (e.g., social anxiety in autism spectrum disorder), autism spectrum disorder, binge eating disorder, alcohol use disorder, treatment resistant depression, major depressive disorder, generalized anxiety disorder, schizophrenia, borderline personality disorder, opioid use disorder, narcissistic personality disorder, avoidant personality disorder, tinnitus, anorexia nervosa, substance use disorder, chronic pain, tobacco addiction, bulimia nervosa, antisocial personality disorder, ADHD, a traumatic brain injury, body dysmorphia, hypoactive sexual desire disorder, migraines, agoraphobia, narcolepsy, obsessive compulsive disorder, and/or fibromyalgia in a subject in need thereof, the methods comprising administering a therapeutically effective amount of a crystalline form of N,N-DMT disclosed herein (e.g., Form III and/or Form IV) or a pharmaceutical composition thereof to the subject.

EXAMPLES

The following example details the preparation and isolation of crystalline forms of N,N-DMT (e.g., Form III and Form IV). The study shows that Form III of N,N-DMT is metastable across all temperatures and to date, Form IV is the most thermodynamically stable polymorph of N,N-DMT having the highest known melting point.

I. Screening Experiments

Screening experiments were performed to identify stable and polymorphic forms of N,N-DMT. The experiments included an exploration of a variety of solvent systems, temperatures, crystallization conditions, and starting materials. Crystallization techniques employed included: slurrying, evaporation, pH swing, vapor diffusion, antisolvent precipitation, vapor stressing and heating. Each of these techniques are explained in greater detail below.

Slurrying: Suspensions were prepared by adding enough solids to a given solvent at the stated conditions so that undissolved solids were present. The mixture was then agitated (typically by stirring or oscillation) in a sealed vial at a given temperature for an extended period of time.

Evaporation: For fast evaporation, solutions were prepared in various solvents and, typically, filtered through a 0.2-μm nylon or PTFE filter. Each solution was allowed to evaporate from an open vial at ambient conditions, unless otherwise stated. For slow evaporation, solutions were prepared in various solvents and, typically, filtered through a 0.2-μm nylon or PTFE filter. Each solution was allowed to evaporate from a covered vial (such as loosely capped or covered with perforated aluminum foil) at ambient conditions.

pH swing experiments were conducted by combining N,N-DMT solids with water with stirring at ambient temperature, resulting in a solution with undissolved solids present. Aliquots of strong acid (e.g., 0.1 N HCIl) were added with stirring, resulting in a clear solution. Aliquots of strong base (e.g., 0.1 N NaOH) were added with stirring, resulting in white suspended solids. In some cases, needles, blades, and aggregates were observed. Crystals were culled and analyzed.

Vapor diffusion: Concentrated solutions were prepared in various solvents and, typically, filtered through a 0.2 μm nylon or PTFE filter. The filtered solution was dispensed into a small vial, which was then placed inside a larger vial containing antisolvent. The small vial was left uncapped, and the larger vial was capped to allow vapor diffusion to occur.

Antisolvent precipitation: Solutions were prepared in various solvents and aliquots of various antisolvents were dispensed with stirring until precipitation occurred. Mixtures were allowed to stir at specified conditions.

Vapor stressing: A small vial containing a given material was placed inside a larger vial containing solvent. The small vial was left uncapped, and the larger vial was capped to allow vapor stressing to occur at the stated temperature.

Heating: Conducted either by DSC (for examination of the thermograms and/or recovery of heated solids for XRPD) or heating on a hot plate/hot bench.

Three anhydrous/unsolvated polymorphs were observed: Forms I, III and IV (Form II reported in the literature was not observed in the screen). A comparison of the properties of the three polymorphic forms of N,N-DMT is provided in Table 1.

TABLE 1

| Comparison of the Properties Form I, II, and IV of N,N-DMT | | | |
|---|---|---|---|
| Characteristics | Form I | Form III | Form IV |
| Physical appearance | White solids | White to off-white solids | White to off-white solids |
| Composition [XRPD] | Successfully indexed, single crystalline phase, consistent with anhydrous/ unsolvated N,N-DMT Form I in literature | Pattern could not be indexed as additional minor peaks observed, except a pattern was obtained from a multi-step heating experiment, which needed recrystallization of melted material at −20° C. | Successfully indexed, consistent with unsolvated N,N-DMT |
| Composition [$^1$H NMR] | Consistent with N,N-DMT, no organic solvent | Consistent w/N,N-DMT, negligible organic solvent | Consistent with N,N-DMT, no organic solvent |
| Melting point (° C.) [DSC] | (a) DSC 10° C./min: endo at 60° C. (onset 58° C.) (b) DSC 2° C./min: endo at 59° C. (onset 58° C.) | (a) DSC 10° C./min: endo at 44° C. (onset 39° C.) (b) DSC 2° C./min: sharp endo 68° C. (onset 67° C.) | (a) DSC 10° C./min: endo at 71° C. (onset 69° C.) (b) DSC 2° C./min: endo 70° C. (onset 69° C.) |
| Aqueous solubility (mg/mL)* | Low (<1) | Not determined | Low (<1) |
| Residual solvent/$H_2O$ [TGA] | 1.0% weight loss up to 240° C. Decomposition, evidenced by a steep drop in the TGA thermogram, begins above approx. 240° C. | 1.4% weight loss 41° C.-201° C. | 1.1% weight loss 50-223° C. |
| Hygroscopicity [DVS] | 0.04 wt % water at 60% RH and 0.18% water at 90% RH; no hysteresis observed | Not determined | — |

Note:
*Solubilities are calculated based on the total solvent used to give a solution; actual solubilities may be greater because of the volume of the solvent portions used or a slow rate of dissolution. Values are rounded to the nearest whole number. If dissolution did not occur as determined by visual assessment, the value is reported as "<".

Figure 19:
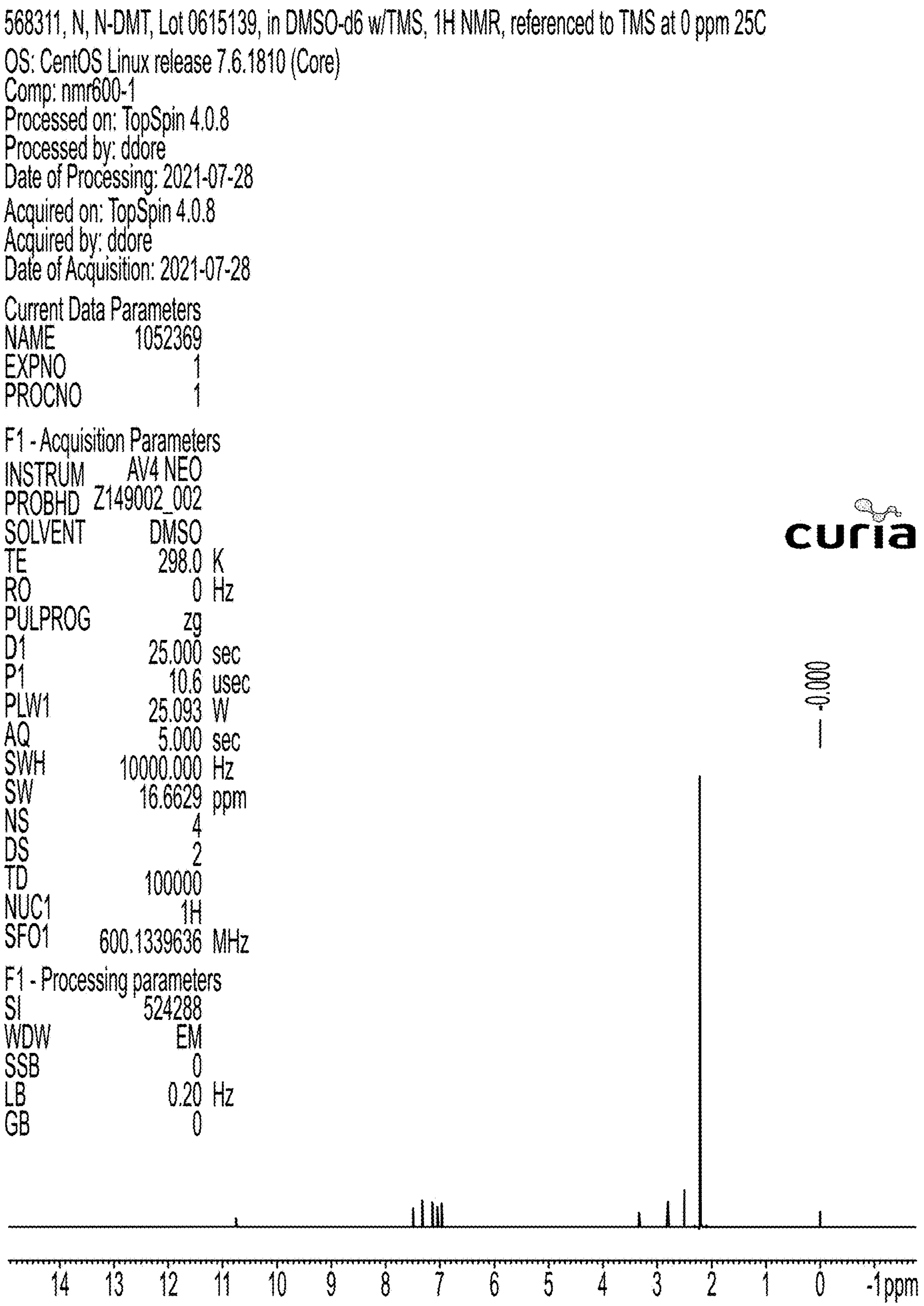
FIG. 19 shows a 1H NMR spectrum for N,N-DMT.

FIG. 19 shows a 1H NMR for N,N-DMT. The 1H NMR spectrum for each of the N,N-DMT samples disclosed herein was substantially the same as shown in FIG. 19.

II. X-ray Powder Diffraction (XRPD) Experiments

XRPD analysis was carried out in transmission geometry and reflection geometry.

XRPD in Transmission Geometry: XRPD patterns were collected with a PANalytical X'Pert PRO MPD or a PANalytical Empyrean diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640f) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5. The data acquisition parameters for each pattern are displayed above the image in the Data section of this report. All images have the instrument labeled as X'Pert PRO MPD regardless of the instrument used.

XRPD in Reflection Geometry

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640f) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 5.5. The data acquisition parameters for each pattern are displayed above the image in the Data section of this report including the divergence slit (DS) and the incident-beam SS.

XRPD peak positions for Forms I, III & IV of N,N-DMT were determined and are enumerated below.

Form I

The XRPD pattern of Form I is shown in FIG. 1. Preferred orientation and particle statistic effects were assessed through comparison to the calculated XRPD pattern from the single crystal structure determination and determined to be negligible.

Observed diffraction peaks are shown in FIG. 1 and enumerated in Table 2, and representative peaks are listed in Table 3.

TABLE 2

| Observed Diffraction Peaks for Form I | | |
|---|---|---|
| °2θ | d space (Å) | Intensity (%) |
| 8.99 ± 0.2 | 9.829 ± 0.218 | 88 |
| 11.98 ± 0.2 | 7.382 ± 0.123 | 77 |
| 12.18 ± 0.2 | 7.261 ± 0.119 | 15 |
| 12.80 ± 0.2 | 6.910 ± 0.108 | 100 |
| 14.48 ± 0.2 | 6.112 ± 0.084 | 23 |
| 15.01 ± 0.2 | 5.898 ± 0.078 | 35 |
| 17.67 ± 0.2 | 5.015 ± 0.056 | 83 |
| 17.82 ± 0.2 | 4.973 ± 0.055 | 51 |
| 18.07 ± 0.2 | 4.905 ± 0.054 | 81 |
| 18.19 ± 0.2 | 4.873 ± 0.053 | 98 |
| 19.82 ± 0.2 | 4.476 ± 0.045 | 68 |
| 20.50 ± 0.2 | 4.329 ± 0.042 | 9 |
| 21.36 ± 0.2 | 4.156 ± 0.038 | 9 |
| 21.73 ± 0.2 | 4.087 ± 0.037 | 7 |
| 22.28 ± 0.2 | 3.987 ± 0.035 | 39 |
| 22.77 ± 0.2 | 3.902 ± 0.034 | 66 |
| 23.22 ± 0.2 | 3.828 ± 0.033 | 9 |
| 23.78 ± 0.2 | 3.739 ± 0.031 | 15 |
| 24.12 ± 0.2 | 3.687 ± 0.030 | 21 |
| 24.27 ± 0.2 | 3.664 ± 0.030 | 10 |
| 24.53 ± 0.2 | 3.626 ± 0.029 | 26 |
| 25.36 ± 0.2 | 3.509 ± 0.027 | 29 |
| 25.68 ± 0.2 | 3.466 ± 0.027 | 5 |
| 25.95 ± 0.2 | 3.431 ± 0.026 | 5 |
| 26.57 ± 0.2 | 3.352 ± 0.025 | 13 |
| 27.25 ± 0.2 | 3.270 ± 0.024 | 59 |
| 27.73 ± 0.2 | 3.215 ± 0.023 | 4 |
| 28.76 ± 0.2 | 3.102 ± 0.021 | 26 |
| 29.21 ± 0.2 | 3.055 ± 0.020 | 3 |
| 29.58 ± 0.2 | 3.017 ± 0.020 | 4 |
| 29.84 ± 0.2 | 2.992 ± 0.020 | 3 |
| 30.54 ± 0.2 | 2.925 ± 0.019 | 22 |
| 31.02 ± 0.2 | 2.881 ± 0.018 | 3 |
| 31.23 ± 0.2 | 2.862 ± 0.018 | 5 |
| 32.32 ± 0.2 | 2.768 ± 0.017 | 5 |
| 32.62 ± 0.2 | 2.743 ± 0.016 | 7 |

TABLE 3

| Representative Diffraction Peaks for Form I | | |
|---|---|---|
| °2θ | d space (Å) | Intensity (%) |
| 8.99 ± 0.2 | 9.829 ± 0.218 | 88 |
| 11.98 ± 0.2 | 7.382 ± 0.123 | 77 |
| 12.80 ± 0.2 | 6.910 ± 0.108 | 100 |
| 14.48 ± 0.2 | 6.112 ± 0.084 | 23 |
| 15.01 ± 0.2 | 5.898 ± 0.078 | 35 |
| 17.67 ± 0.2 | 5.015 ± 0.056 | 83 |
| 17.82 ± 0.2 | 4.973 ± 0.055 | 51 |
| 18.07 ± 0.2 | 4.905 ± 0.054 | 81 |
| 18.19 ± 0.2 | 4.873 ± 0.053 | 98 |
| 19.82 ± 0.2 | 4.476 ± 0.045 | 68 |
| 22.28 ± 0.2 | 3.987 ± 0.035 | 39 |
| 22.77 ± 0.2 | 3.902 ± 0.034 | 66 |
| 24.53 ± 0.2 | 3.626 ± 0.029 | 26 |
| 25.36 ± 0.2 | 3.509 ± 0.027 | 29 |
| 27.25 ± 0.2 | 3.270 ± 0.024 | 59 |
| 28.76 ± 0.2 | 3.102 ± 0.021 | 26 |
| 30.54 ± 0.2 | 2.925 ± 0.019 | 22 |

Form III

Preferred orientation and particle statistic effects were assessed through comparison to XRPD patterns obtained from diffractometers in different geometries and found to be significant. Observed diffraction peaks are shown in FIG. 2 and enumerated in Table 4, and prominent diffraction peaks are listed in Table 5. Note that none of the peaks are known to be representative or characteristic of this material since the state of preferred orientation in this sample is not known.

TABLE 4

| Observed Diffraction Peaks for Form III | | |
|---|---|---|
| °2θ | d space (Å) | Intensity (%) |
| 7.62 ± 0.2 | 11.592 ± 0.304 | 76 |
| 15.24 ± 0.2 | 5.809 ± 0.076 | 100 |
| 16.81 ± 0.2 | 5.270 ± 0.062 | 2 |
| 19.22 ± 0.2 | 4.614 ± 0.048 | 9 |
| 19.59 ± 0.2 | 4.528 ± 0.046 | 5 |
| 20.05 ± 0.2 | 4.425 ± 0.044 | 1 |
| 20.43 ± 0.2 | 4.344 ± 0.042 | 2 |
| 20.68 ± 0.2 | 4.292 ± 0.041 | 2 |
| 21.48 ± 0.2 | 4.134 ± 0.038 | 1 |
| 22.41 ± 0.2 | 3.964 ± 0.035 | 2 |
| 22.93 ± 0.2 | 3.875 ± 0.033 | 7 |
| 23.14 ± 0.2 | 3.841 ± 0.033 | 2 |
| 26.29 ± 0.2 | 3.387 ± 0.025 | 1 |
| 27.14 ± 0.2 | 3.283 ± 0.024 | 1 |
| 27.82 ± 0.2 | 3.204 ± 0.023 | 1 |
| 28.49 ± 0.2 | 3.130 ± 0.022 | 1 |
| 30.71 ± 0.2 | 2.909 ± 0.018 | 3 |
| 31.56 ± 0.2 | 2.833 ± 0.017 | 1 |

TABLE 5

| Representative Diffraction Peaks for Form III | | |
|---|---|---|
| °2θ | d space (Å) | Intensity (%) |
| 7.62 ± 0.2 | 11.592 ± 0.304 | 76 |
| 15.24 ± 0.2 | 5.809 ± 0.076 | 100 |
| 19.22 ± 0.2 | 4.614 ± 0.048 | 9 |
| 19.59 ± 0.2 | 4.528 ± 0.046 | 5 |
| 22.93 ± 0.2 | 3.875 ± 0.033 | 7 |

Form IV

Preferred orientation and particle statistic effects were assessed through comparison to the calculated XRPD pattern from the single crystal structure determination and determined to be negligible. Observed peaks are shown in FIG. 3 and enumerated in Table 6, and representative peaks are listed in Table 7.

TABLE 6

| Observed Diffraction Peaks for Form IV | | |
|---|---|---|
| °2θ | d space (Å) | Intensity (%) |
| 7.68 ± 0.2 | 11.502 ± 0.299 | 5 |
| 10.35 ± 0.2 | 8.540 ± 0.165 | 2 |
| 11.92 ± 0.2 | 7.419 ± 0.124 | 5 |
| 13.05 ± 0.2 | 6.779 ± 0.103 | 5 |
| 13.61 ± 0.2 | 6.501 ± 0.095 | 100 |
| 13.89 ± 0.2 | 6.370 ± 0.091 | 29 |
| 13.99 ± 0.2 | 6.325 ± 0.090 | 25 |
| 15.16 ± 0.2 | 5.840 ± 0.077 | 5 |
| 15.39 ± 0.2 | 5.753 ± 0.074 | 22 |
| 16.16 ± 0.2 | 5.480 ± 0.067 | 11 |
| 16.90 ± 0.2 | 5.242 ± 0.062 | 10 |
| 17.45 ± 0.2 | 5.078 ± 0.058 | 9 |
| 17.76 ± 0.2 | 4.990 ± 0.056 | 57 |
| 18.05 ± 0.2 | 4.911 ± 0.054 | 17 |
| 18.64 ± 0.2 | 4.756 ± 0.051 | 42 |
| 19.25 ± 0.2 | 4.607 ± 0.047 | 6 |
| 19.81 ± 0.2 | 4.478 ± 0.045 | 4 |
| 20.79 ± 0.2 | 4.269 ± 0.041 | 100 |
| 21.11 ± 0.2 | 4.205 ± 0.039 | 11 |
| 21.63 ± 0.2 | 4.105 ± 0.038 | 17 |
| 22.39 ± 0.2 | 3.968 ± 0.035 | 15 |
| 22.69 ± 0.2 | 3.916 ± 0.034 | 12 |

TABLE 6-continued

| Observed Diffraction Peaks for Form IV | | |
|---|---|---|
| °2θ | d space (Å) | Intensity (%) |
| 23.59 ± 0.2 | 3.768 ± 0.031 | 28 |
| 23.81 ± 0.2 | 3.734 ± 0.031 | 4 |
| 24.47 ± 0.2 | 3.635 ± 0.029 | 21 |
| 24.77 ± 0.2 | 3.591 ± 0.029 | 10 |
| 25.22 ± 0.2 | 3.528 ± 0.028 | 5 |
| 26.06 ± 0.2 | 3.417 ± 0.026 | 23 |
| 26.66 ± 0.2 | 3.341 ± 0.025 | 24 |
| 26.90 ± 0.2 | 3.312 ± 0.024 | 3 |
| 27.53 ± 0.2 | 3.237 ± 0.023 | 2 |
| 27.99 ± 0.2 | 3.185 ± 0.022 | 5 |
| 28.23 ± 0.2 | 3.159 ± 0.022 | 4 |
| 28.61 ± 0.2 | 3.118 ± 0.021 | 3 |
| 28.75 ± 0.2 | 3.103 ± 0.021 | 3 |
| 29.28 ± 0.2 | 3.048 ± 0.020 | 3 |
| 29.46 ± 0.2 | 3.030 ± 0.020 | 2 |
| 29.63 ± 0.2 | 3.013 ± 0.020 | 2 |
| 30.17 ± 0.2 | 2.960 ± 0.019 | 2 |
| 30.36 ± 0.2 | 2.942 ± 0.019 | 3 |
| 30.59 ± 0.2 | 2.920 ± 0.019 | 3 |
| 30.91 ± 0.2 | 2.891 ± 0.018 | 4 |
| 31.09 ± 0.2 | 2.874 ± 0.018 | 8 |
| 31.63 ± 0.2 | 2.826 ± 0.017 | 3 |
| 31.88 ± 0.2 | 2.805 ± 0.017 | 4 |
| 32.83 ± 0.2 | 2.726 ± 0.016 | 2 |
| 33.21 ± 0.2 | 2.695 ± 0.016 | 2 |
| 33.74 ± 0.2 | 2.654 ± 0.015 | 2 |
| 34.45 ± 0.2 | 2.601 ± 0.015 | 2 |
| 35.31 ± 0.2 | 2.540 ± 0.014 | 2 |

TABLE 7

| Representative Diffraction Peaks for Form IV | | |
|---|---|---|
| °2θ | d space (Å) | Intensity (%) |
| 13.61 ± 0.2 | 6.501 ± 0.095 | 100 |
| 13.89 ± 0.2 | 6.370 ± 0.091 | 29 |
| 13.99 ± 0.2 | 6.325 ± 0.090 | 25 |
| 15.39 ± 0.2 | 5.753 ± 0.074 | 22 |
| 17.76 ± 0.2 | 4.990 ± 0.056 | 57 |
| 18.64 ± 0.2 | 4.756 ± 0.051 | 42 |
| 20.79 ± 0.2 | 4.269 ± 0.041 | 100 |
| 23.59 ± 0.2 | 3.768 ± 0.031 | 28 |
| 24.47 ± 0.2 | 3.635 ± 0.029 | 21 |
| 26.06 ± 0.2 | 3.417 ± 0.026 | 23 |
| 26.66 ± 0.2 | 3.341 ± 0.025 | 24 |

III. Single Crystal XRD Experiments

Single crystal structures were afforded for Forms I and IV as described below.

Preparation of Samples for Single Crystal XRD:

Form I: N,N-DMT solids (83.7 mg) were combined with water (2 mL) with stirring at ambient temperature, resulting in a solution with undissolved solids present. Aliquots of 0.1 N HCl, totaling 10.5 mL, were added with stirring, resulting in a clear solution. Aliquots of 0.1 N NaOH, totaling 11.5 mL, were added with stirring, resulting in white suspended solids. Needles, blades, and aggregates were observed. A crystal was culled and analyzed.

Form IV: N,N-DMT solids (102.01 mg) were combined with heptane (1 mL) with stirring at ~40° C., resulting in a solution with undissolved solids present. The slurry was left to stir at ~40° C. for 12 days, after which thick birefringent needles were observed. A crystal was culled and analyzed.

Single Crystal XRD Data Collection:

Form I: A colorless block having approximate dimensions of 0.18×0.11×0.06 $mm^3$, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3R 200K hybrid pixel array detector.

Cell constants and an orientation matrix for data collection were obtained from least-squares refinement using the setting angles of 2590 reflections in the range 4.4940°<θ<75.3650°. The space group was determined by the program CRYSALISPRO to be P21/c (international tables no. 14). The data were collected to a maximum diffraction angle (2θ) of 151.432° at room temperature.

Form IV: A colorless block having approximate dimensions of 0.17×0.15×0.06 $mm^3$, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector.

Cell constants and an orientation matrix for data collection were obtained from least-squares refinement using the setting angles of 5465 reflections in the range 3.8290°<θ<74.9960°. The space group was determined by the program CRYSALISPRO to be P21/n (international tables no. 14). The data were collected to a maximum diffraction angle (2θ) of 151.584° at room temperature.

The single crystal data obtained from Forms I and IV are enumerated below in Table 8.

TABLE 8

| Single Crystal Data of Polymorphic Forms I & IV of N,N-DMT | | |
|---|---|---|
| Crystal data | Form I | Form IV |
| Crystal system | monoclinic | monoclinic |
| Space group | $P2_1/c$ | $P2_1/n$ |
| Cell parameters | a = 7.4379(2) Å | a = 7.8301(2) Å |
| | b = 19.6312(4) Å | b = 22.9828(4) Å |
| | c = 7.8759(2) Å | c = 12.7380(2) Å |
| | α = 90° | α = 90° |
| | β = 97.857(3)° | β = 91.980(2)° |
| | γ = 90° | γ = 90° |
| Unit cell volume (Å3) | 1139.20(5) | 2290.93(8) |

Note:
Standard uncertainty is written in crystallographic parenthesis notation, e.g. 0.123(4) is equivalent to 0.123 ± 0.004.

Figure 4:
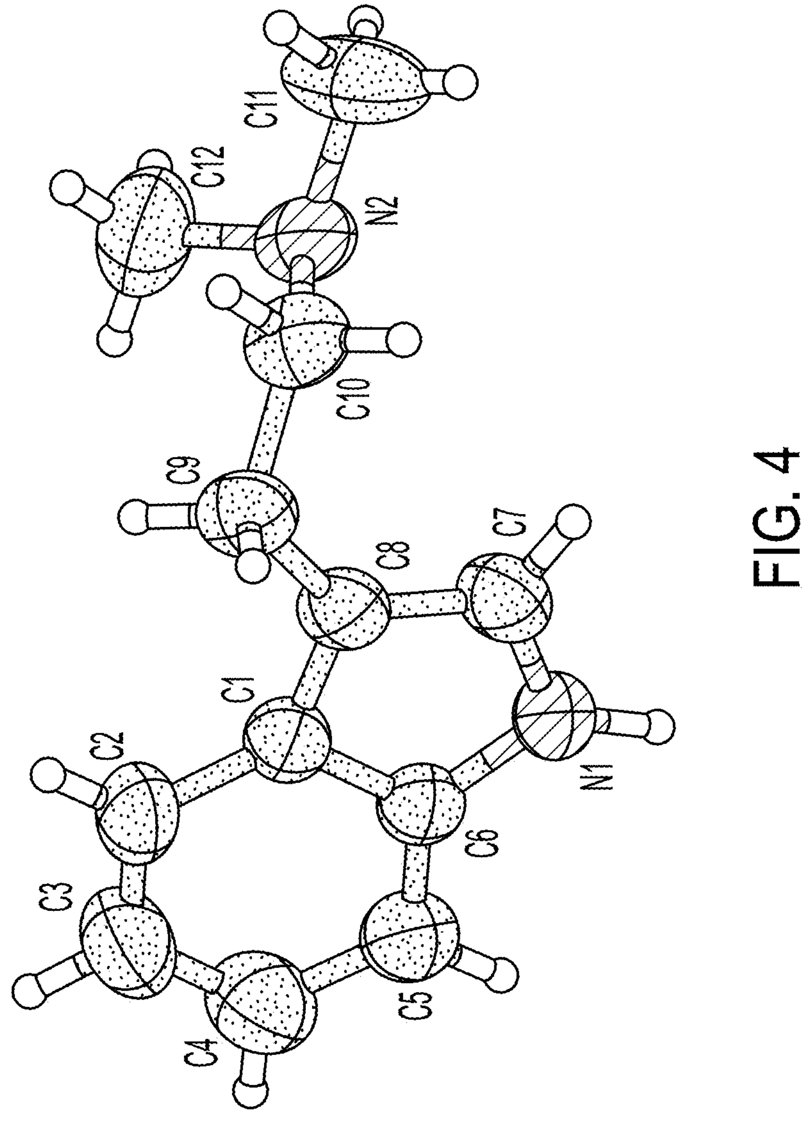
FIG. 4 shows an atomic displacement ellipsoid diagram of Form I of N,N-DMT.
Figure 5:
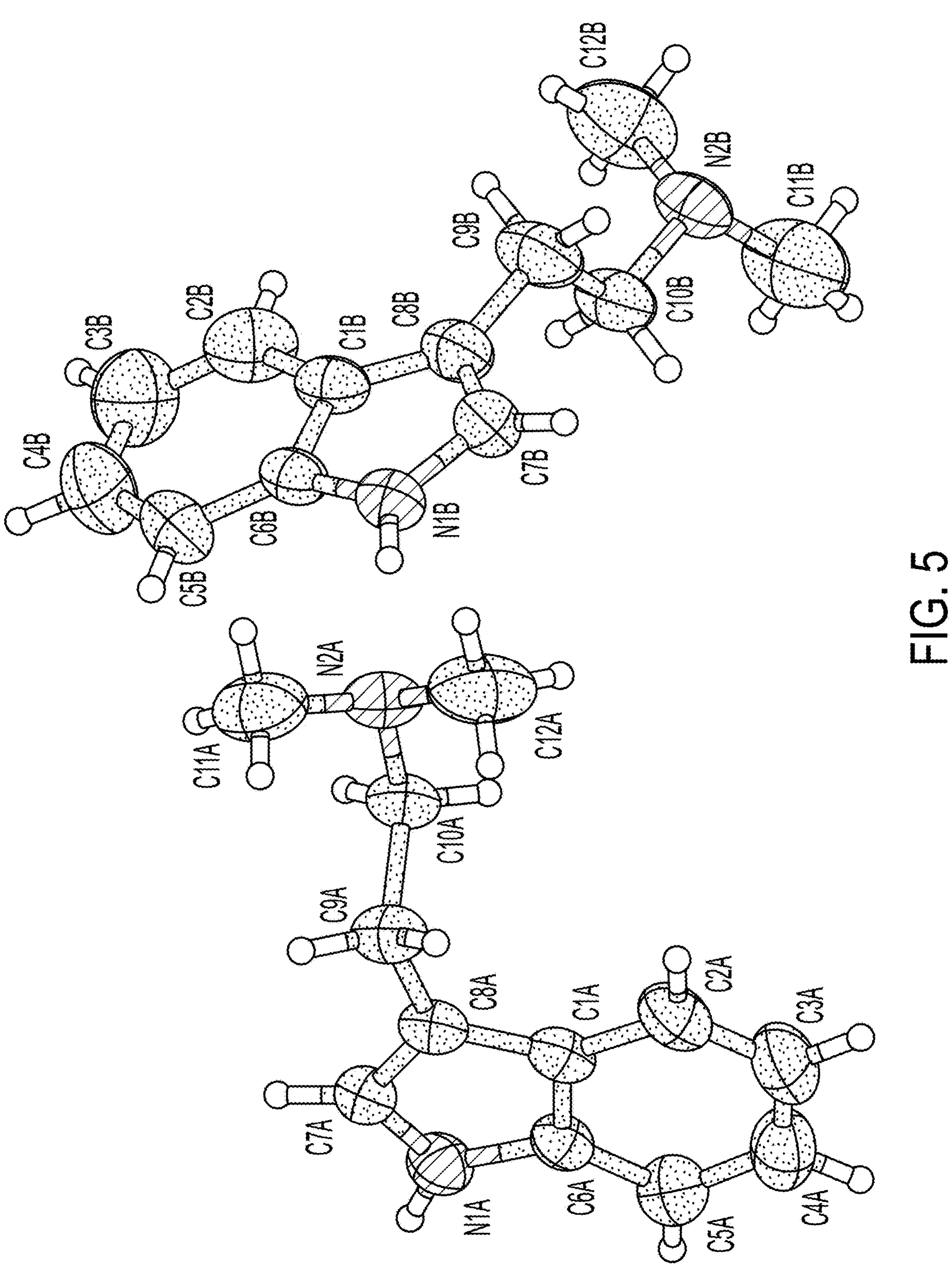
FIG. 5 shows an atomic displacement ellipsoid diagram of Form IV of N,N-DMT.

Atomic displacement ellipsoid diagrams of N,N-DMT for Form I and Form IV are shown in FIG. 4 and FIG. 5, respectively.

IV. Thermal Behavior Experiments

Differential Scanning Calorimetry (DSC):

DSC was performed using a Mettler-Toledo DSC3+ differential scanning calorimeter. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, the weight was accurately recorded, and the sample was inserted into the DSC cell. A weighed aluminum pan configured as the sample pan was placed on the reference side of the cell. The pan lid was pierced prior to sample analysis. The samples were analyzed from −25° C. to 250° C. at 10° C./min unless otherwise stated.

Thermogravimetric and Differential Scanning Calorimetry (TGA or TGA/DSC)

TGA or TGA/DSC analyses were performed using a Mettler-Toledo TGA/DSC3+ analyzer. Temperature and enthalpy adjustments were performed using indium, tin, zinc, and phenyl salicylate, and then verified with indium. The balance was verified with calcium oxalate. The sample was placed in an aluminum pan. The pan was hermetically sealed, the lid pierced, and the pan was then inserted into the TG furnace. A weighed aluminum pan configured as the sample pan was placed on the reference platform. The furnace was heated under nitrogen. Samples were analyzed from 25° C. to 350° C. at 10° C./min. Thermogravimetric analyses typically experience a period of equilibration at the start of each analysis, indicated by parentheses on the thermograms in the Figures section (V). The starting temperature for relevant weight loss calculations is selected at a point beyond this region (typically above 35° C.) for accuracy.

Figure 6:
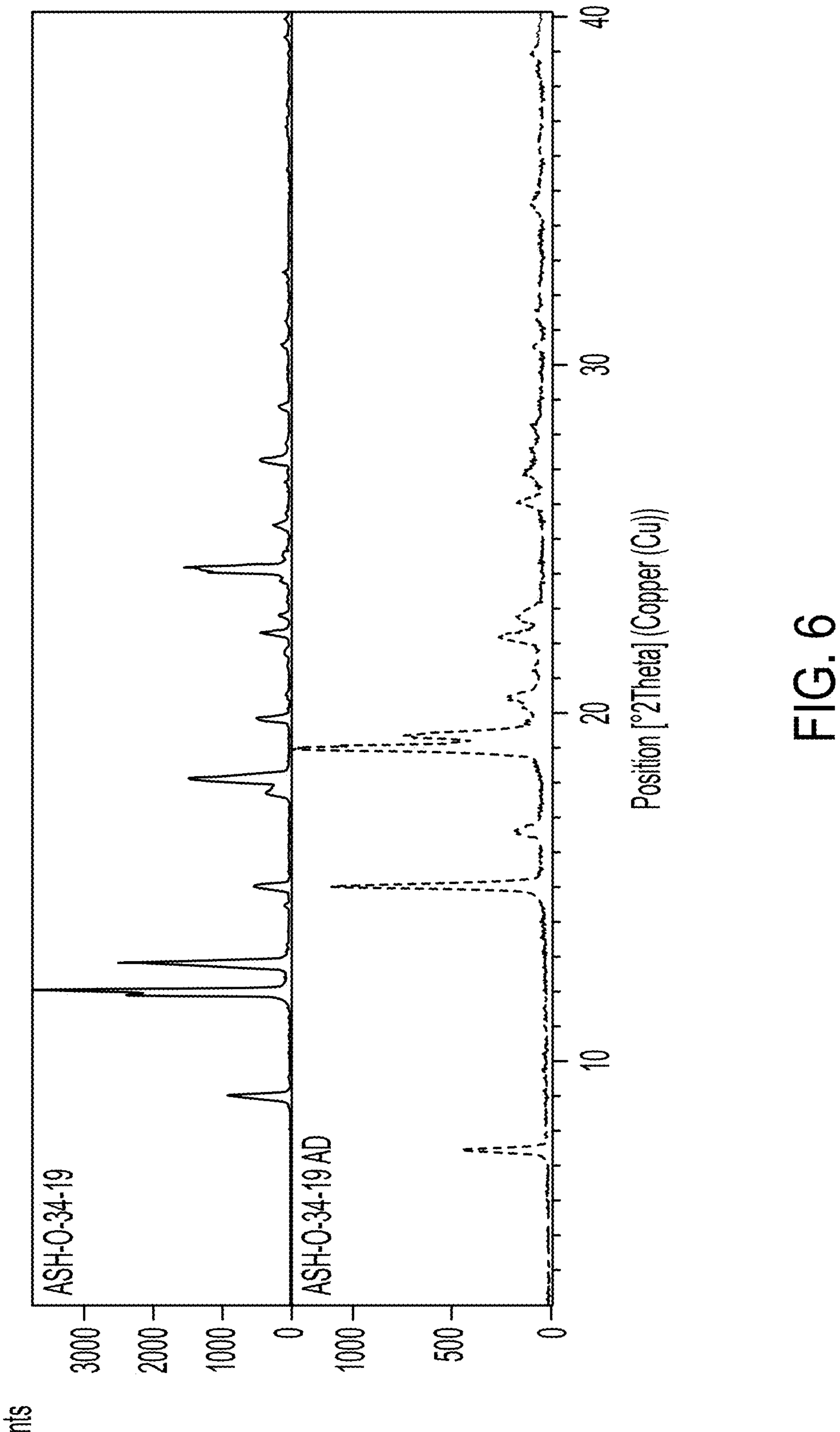
FIG. 6 shows the XRPD diffractogram of a sample of the Form I of N,N-DMT before (top plot) and after (bottom plot) dynamic vapor sorption (DVS).
Figure 7:
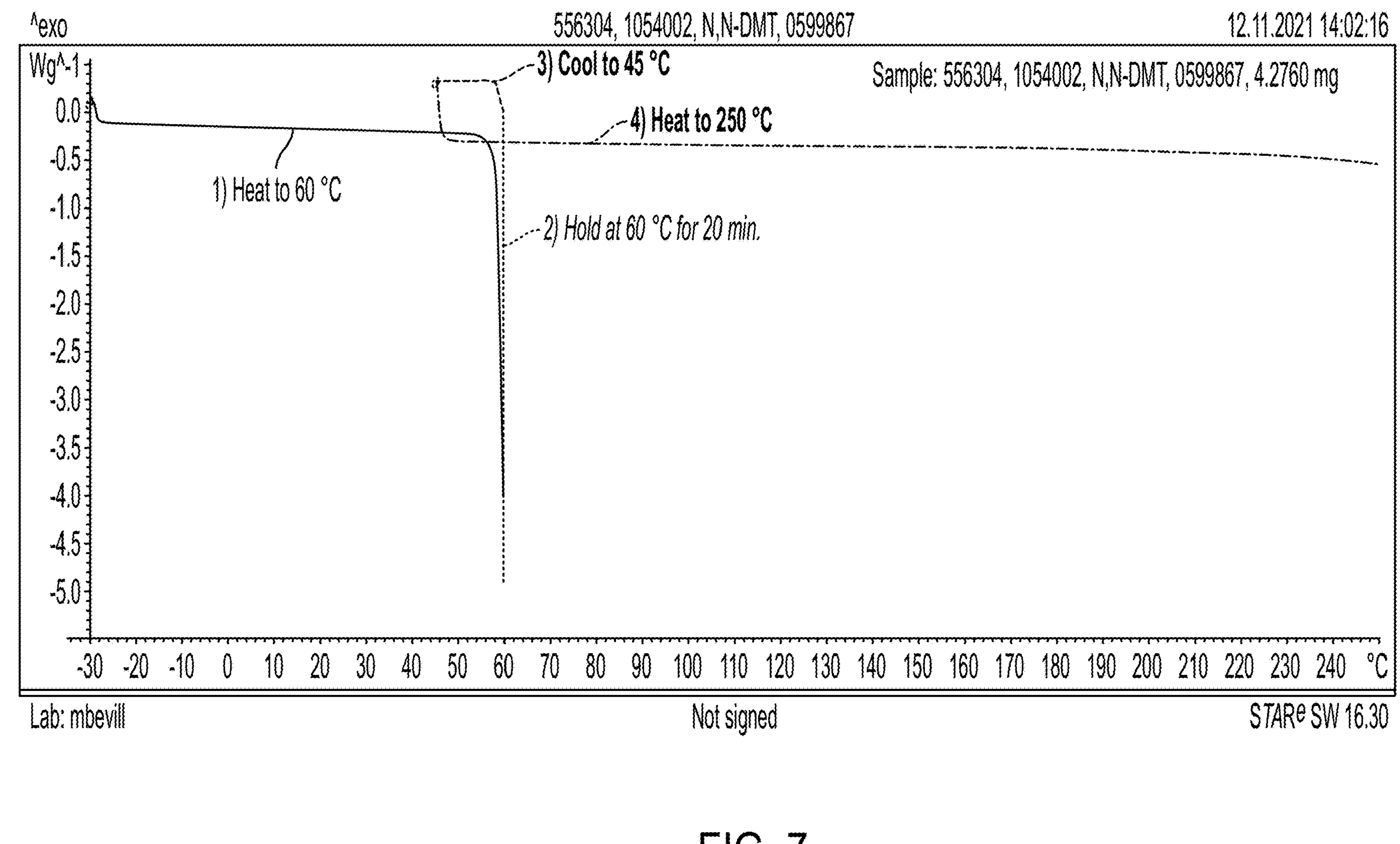
FIGS. 7 and 8 show DCS thermograms of a sample of Form I of N,N-DMT.

Form I:

A DVS cycle study on N,N-DMT Form I had exhibited a form change when dried at 60° C. (as a final step of drying the API during manufacture) (FIG. 6). To study this behavior further, solid state cycling DSC thermograms for Form I were collected (FIG. 7). FIG. 7 is a thermogram for a sample that was initially heated to 60° C., causing the solids to melt. The melted material was held at 60° C. for 20 minutes, then cooled to 45° C. and reheated to 250° C. No significant events, such as recrystallization or melting of a higher-melting form, were observed.

Figure 8:
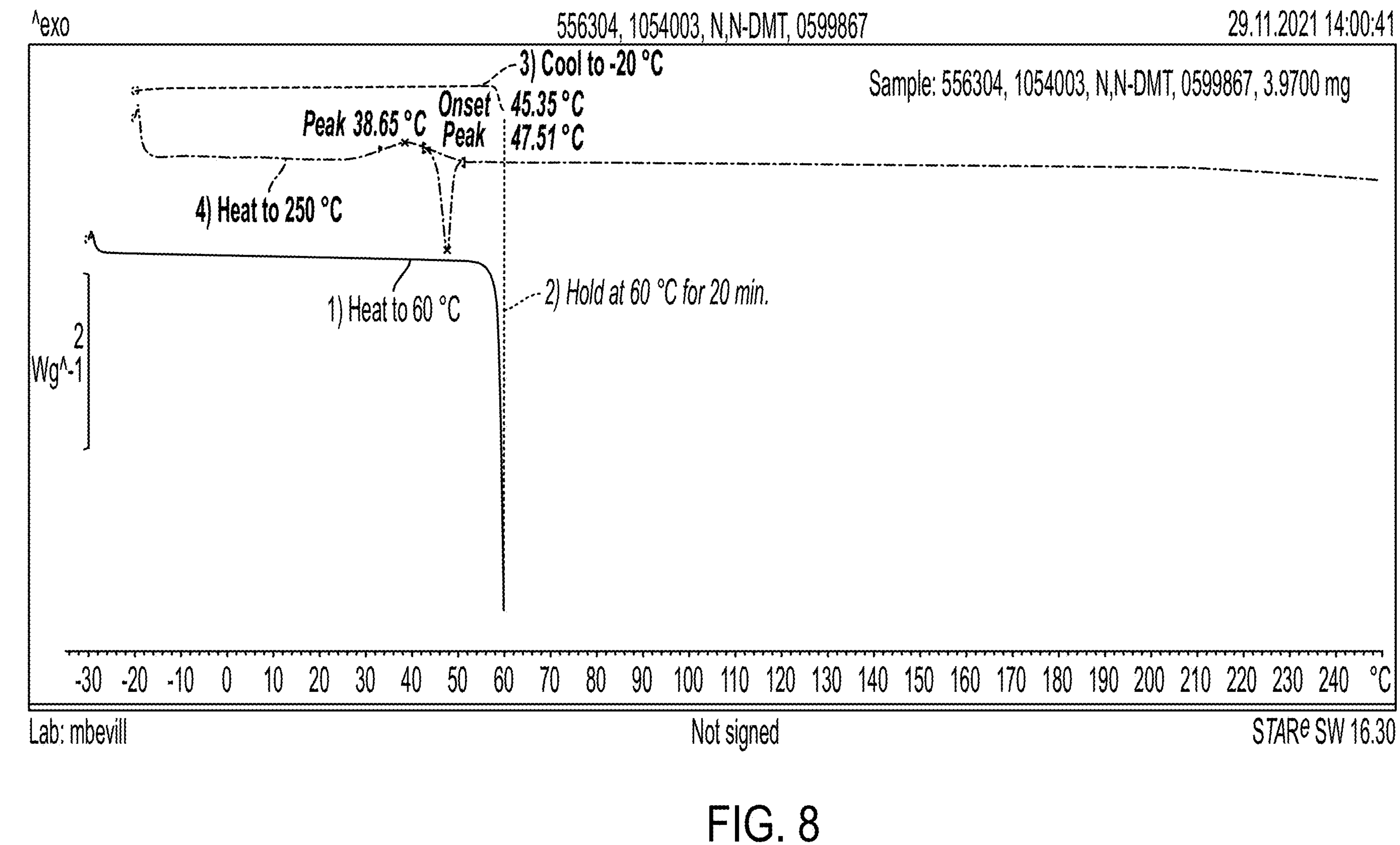

A similar experiment was conducted, but the melted material was cooled down to −20° C. before being reheated to 250° C. (FIG. 8). In this experiment, an exotherm is observed around 39° C. in the final heating step, consistent with crystallization, and is followed immediately by an endotherm at approximately 45° C. (onset), indicative of melting. This melting point is similar to that observed for Form III. The DSC experiments indicate that drying of the post-DVS solids at 60° C. melted the material, and then it recrystallized upon cooling to ambient temperature to lower-melting Form III.

Figure 9:
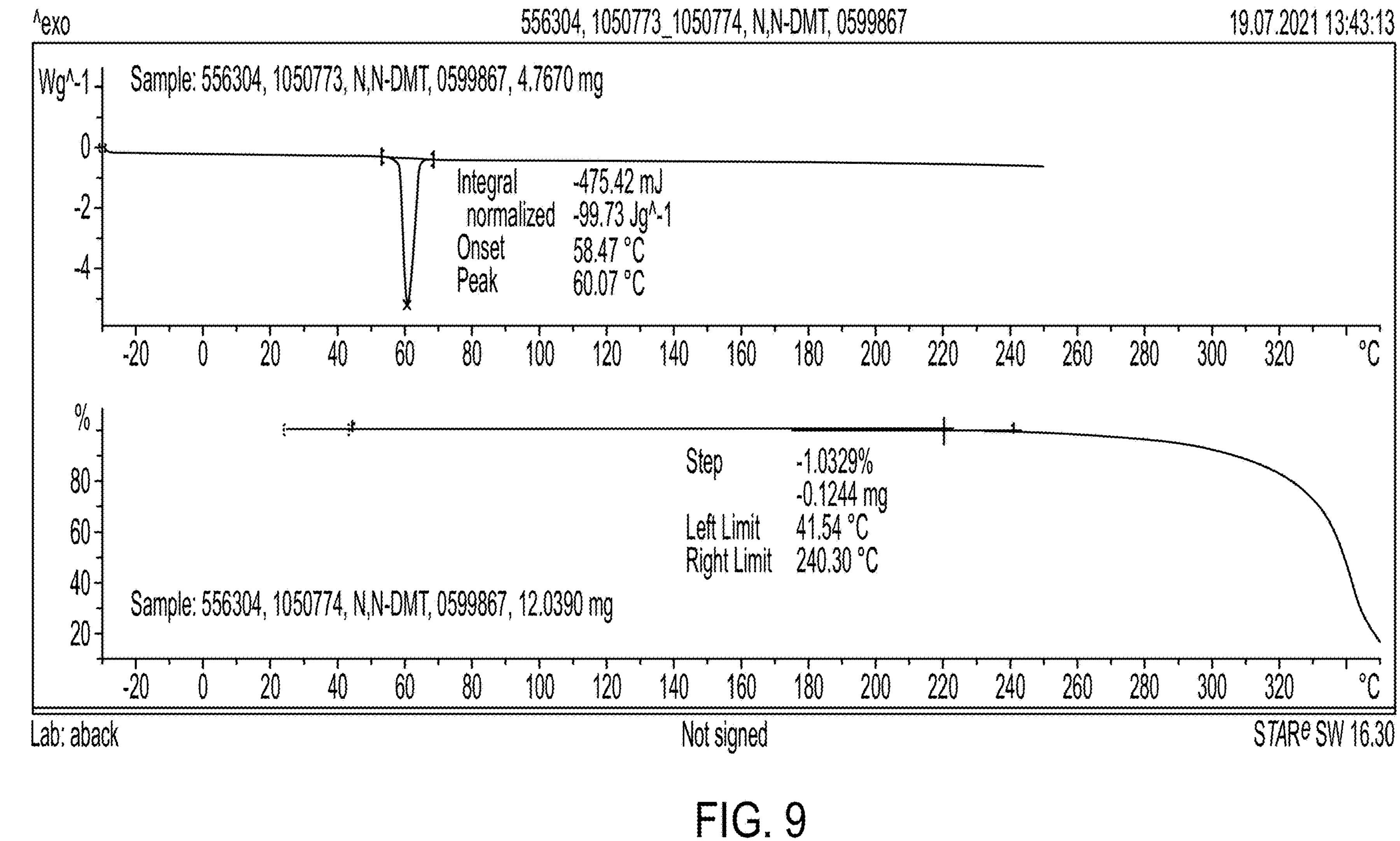
FIG. 9 shows a DSC thermogram (top) collected at a heating rate of 10° C./minute and a TGA thermogram (bottom) of a sample of Form I of N,N-DMT.
Figure 10:
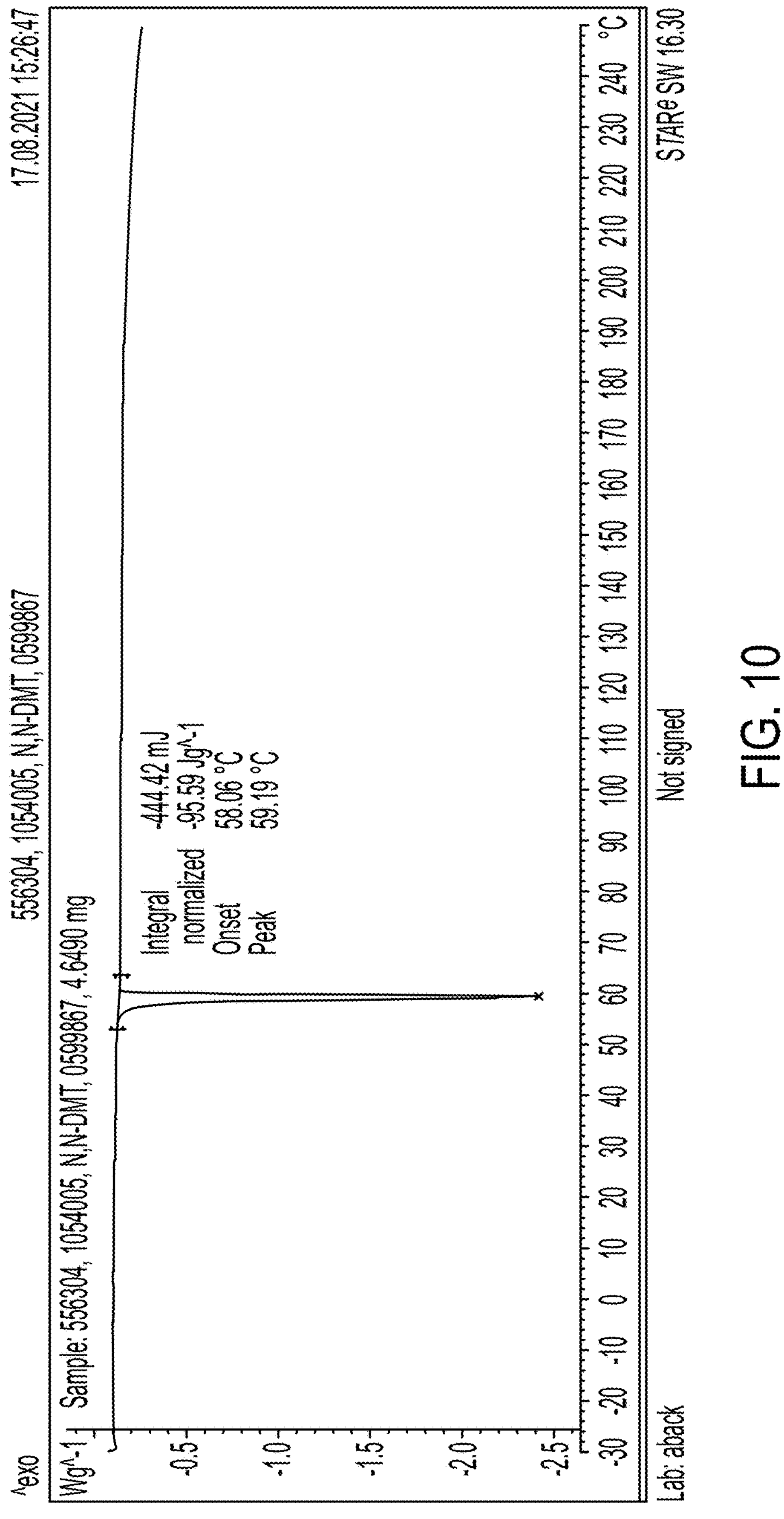
FIG. 10 shows a DSC thermogram collected at a heating rate of 2° C./minute of a sample of Form I of N,N-DMT.

DSC and TGA thermograms for Form I were also collected at the standard 10° C./minute heating rate (FIG. 9). An additional DSC thermogram was obtained at a slower heating rate (2° C./minute) to obtain more sensitive data (FIG. 10).

A melting endotherm is observed in both thermograms at 58° C. (onset), consistent with the melting point reported for Form I in literature. The TGA thermogram exhibits only 1.0% weight loss up to 240° C., consistent with an anhydrous/unsolvated material. Decomposition, evidenced by a steep drop in the TGA thermogram, begins above approximately 240° C.

Figure 11:
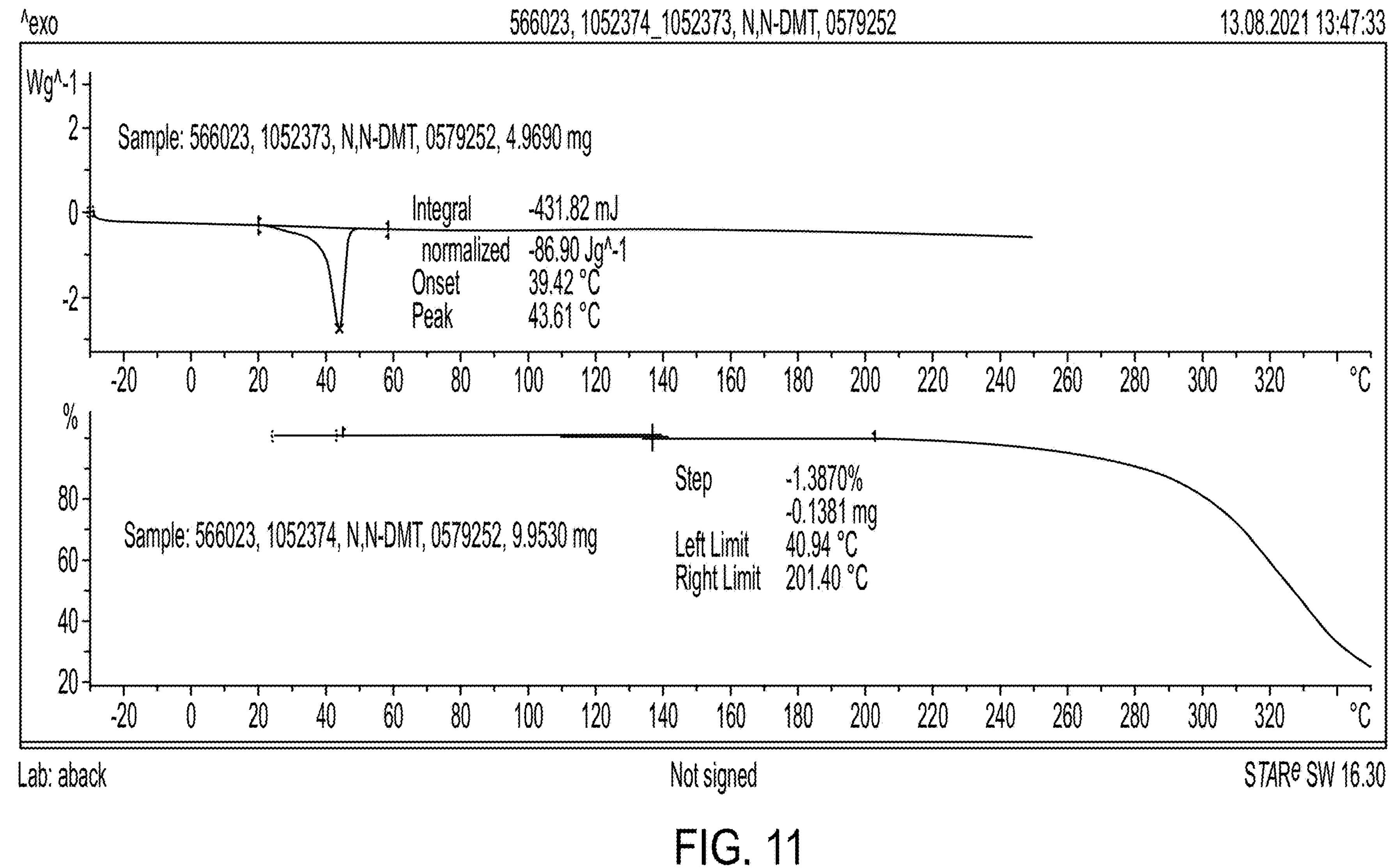
FIG. 11 shows a DSC thermogram (top) collected at a heating rate of 10° C./minute and a TGA thermogram (bottom) of a sample of Form III of N,N-DMT.
Figure 12:
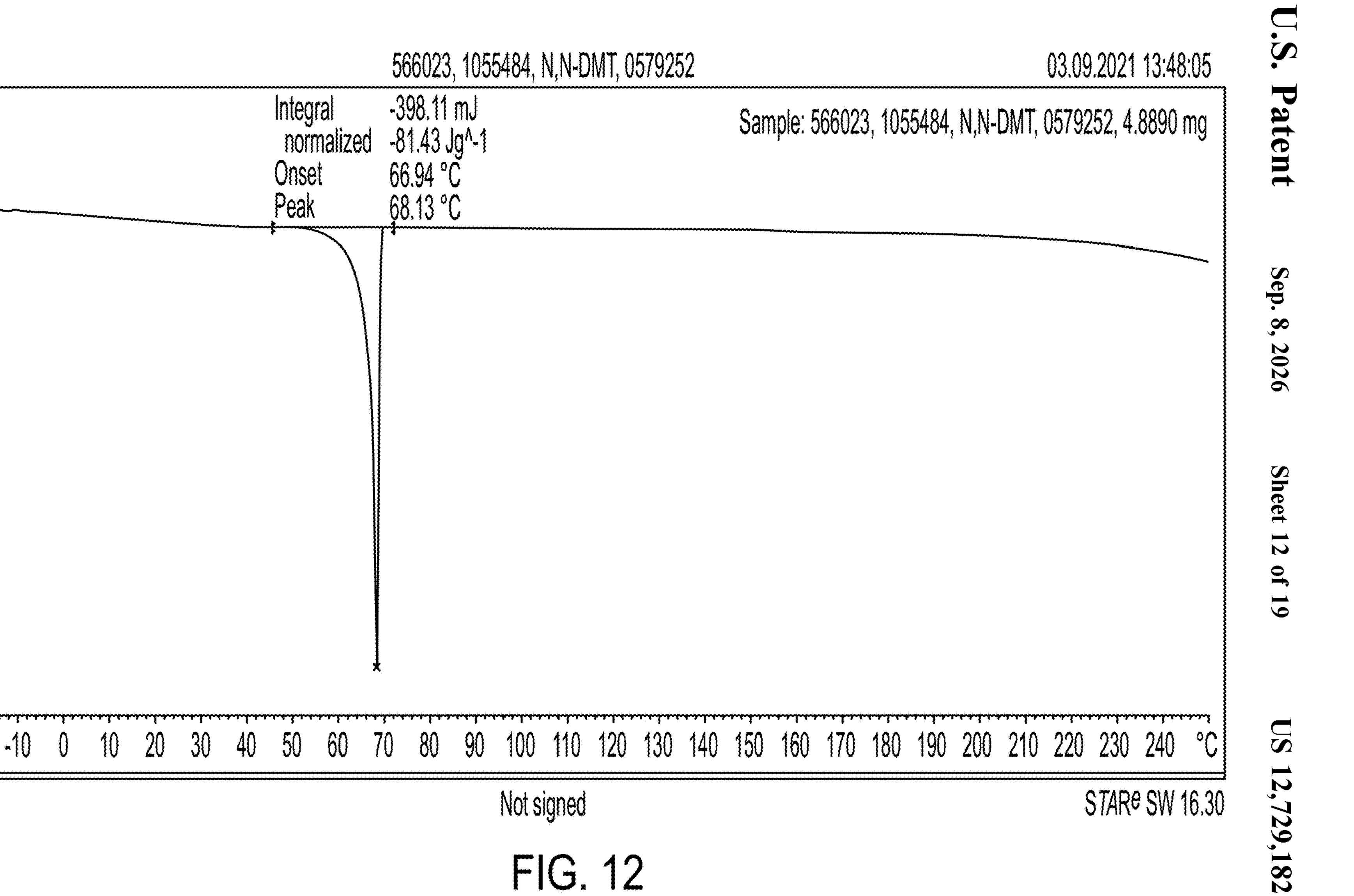
FIG. 12 shows a DSC thermogram collected at a heating rate of 2° C./minute of a sample of Form III of N,N-DMT.

Form III:

DSC and TGA thermograms, collected at a heating rate of 10° C. per minute (FIG. 11). A melting endotherm is observed by DSC at 39° C. (onset). Negligible weight loss by TGA up to 201° C. is consistent with an anhydrous/unsolvated material. Decomposition is observed above approximately 240° ° C. To obtain more sensitive data, DSC thermograms were collected at a heating rate of 2° C. per minute (FIG. 12). In FIG. 12, when the ramping rate was brought down to 2 C/min, the crystallization (into another form) and melt of form III are simultaneous due to the low temp ramping rate. Based on the endotherm with a melting onset at 66.94° C., we can conclude that form III had time to melt then recrystallize into form IV which melted around 67° C.

Figure 13:
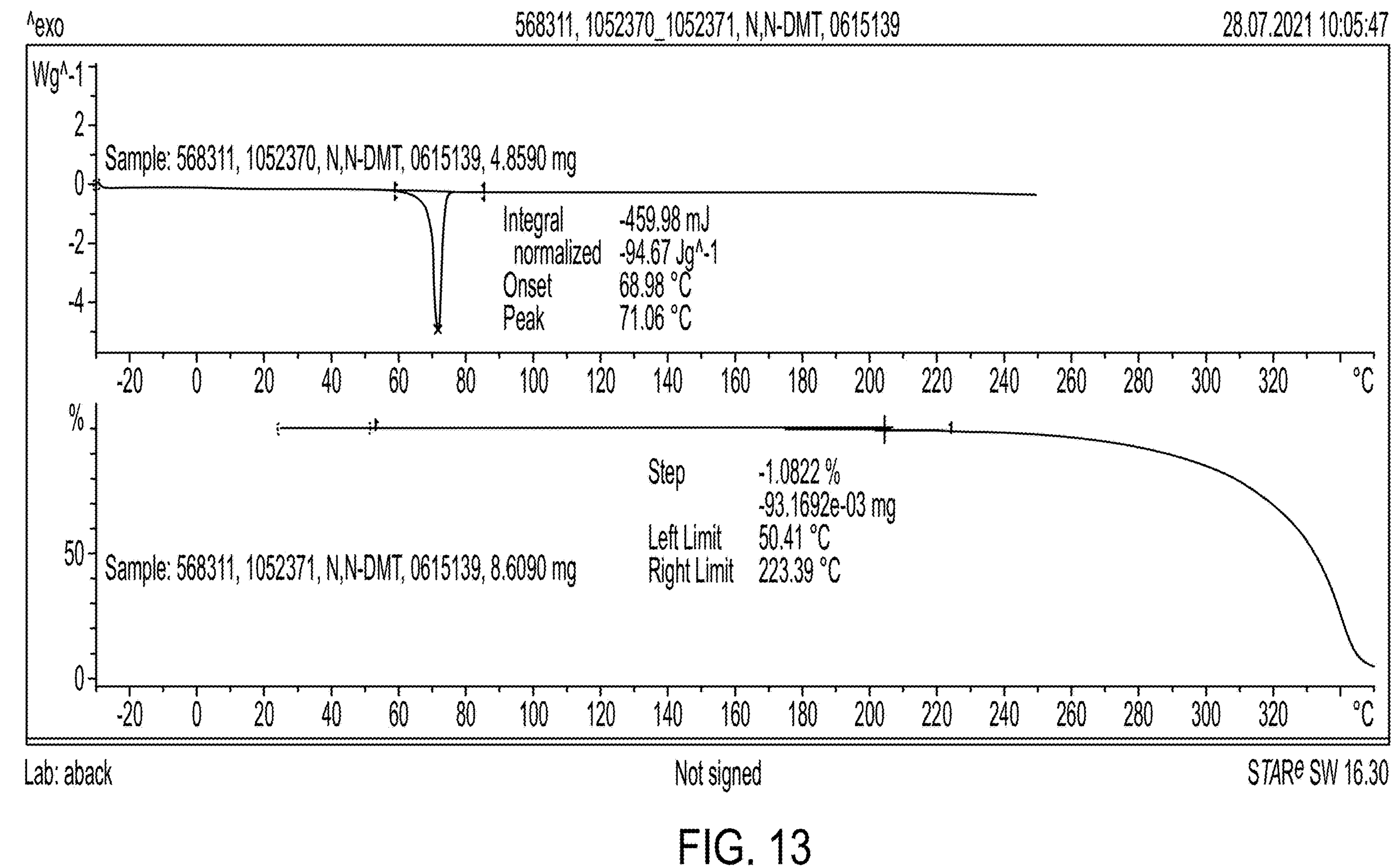
FIG. 13 shows a DSC thermogram (top) collected at a heating rate of 10° C./minute and a TGA thermogram (bottom) of a sample of Form IV of N,N-DMT.

Solid state heating experiments were also conducted starting with Form III (+ a minor unknown component) (FIG. 13). These experiments were designed to observe melting and recrystallization behavior at a variety of temperatures. Approximate melt onset temperature for Form III (39° C.) from DSC characterization was used as a basis for determining form conversions.

Form III was observed to concurrently melt and recrystallize to Form IV when held between 35° C. and 40° C. However, when melted material was cooled to RT or −20° C., it recrystallized to Form III in some cases. In one experiment, melted material did not exhibit signs of crystallization upon standing in the freezer for 1 day, so heptane was added, and the sample was left to stir in the freezer for 12 days, resulting in crystallization to Form IV.

Figure 14:
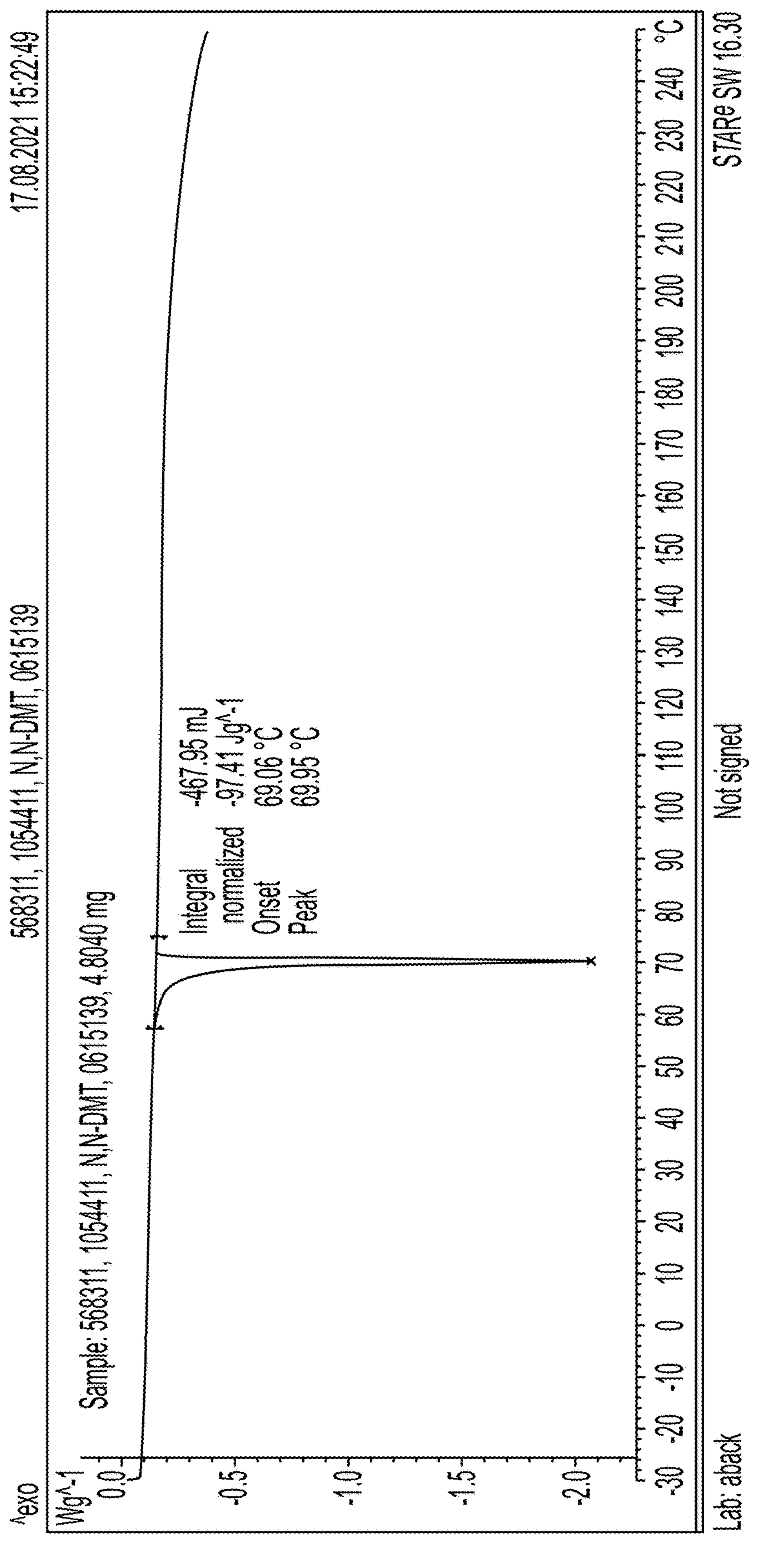
FIG. 14 shows a DSC thermogram (top) collected at a heating rate of 10° C./minute and a TGA thermogram (bottom) of a sample of Form IV of N,N-DMT.
Figure 15:
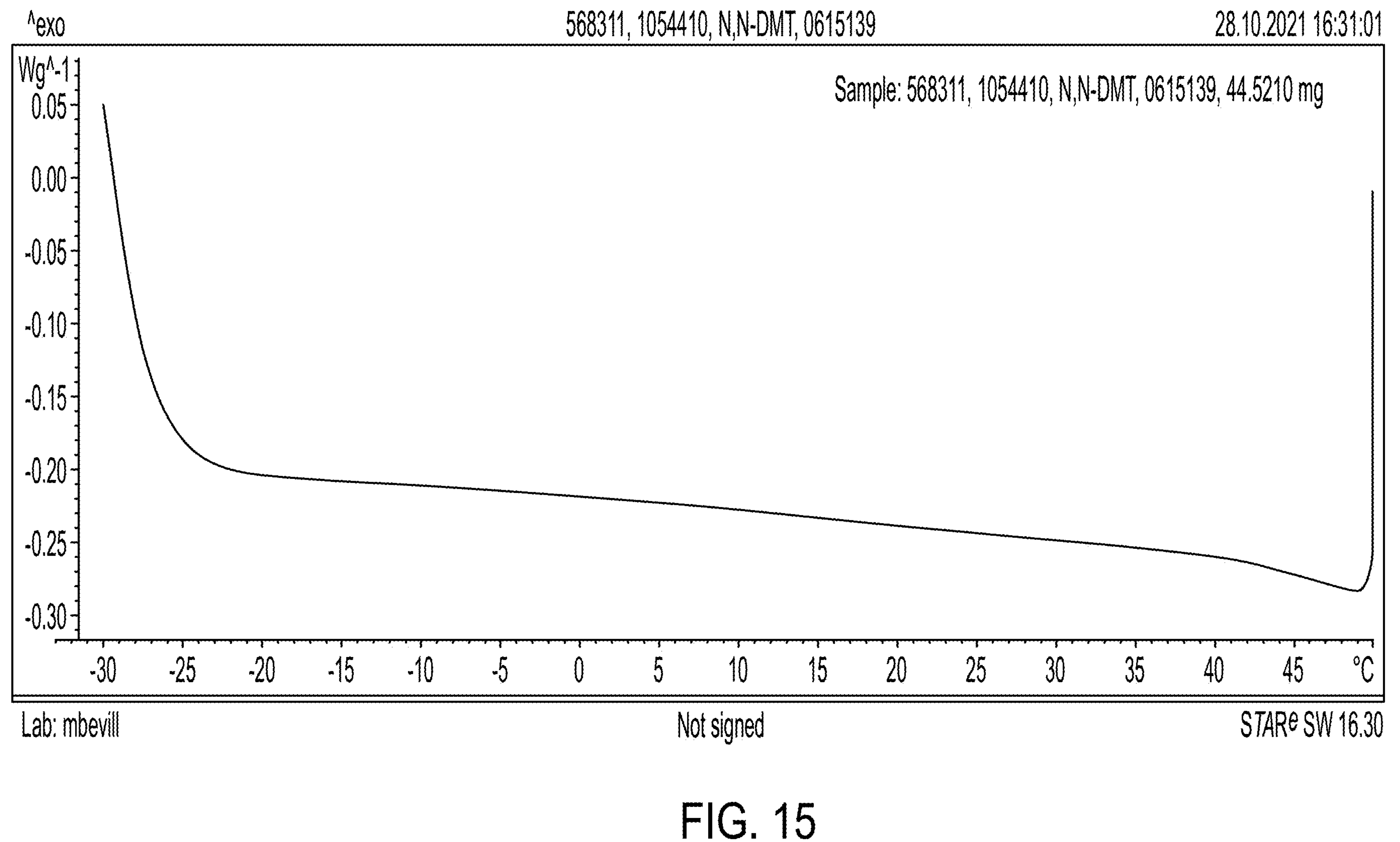
FIG. 15 shows a DSC thermogram collected at a heating rate of 2° C./minute of a sample of Form IV of N,N-DMT.

Form IV:

DSC and TGA thermograms were collected at a heating rate of 10° C./min, and an additional DSC thermogram was obtained at 2° C./min (FIG. 14 and FIG. 15, respectively). Both DSC thermograms exhibit a sharp melting endotherm at an onset of 69° C. Negligible weight loss up to 223° ° C. by TGA is consistent with an anhydrous/unsolvated material. Decomposition is observed above approximately 240° C.

Figure 16:
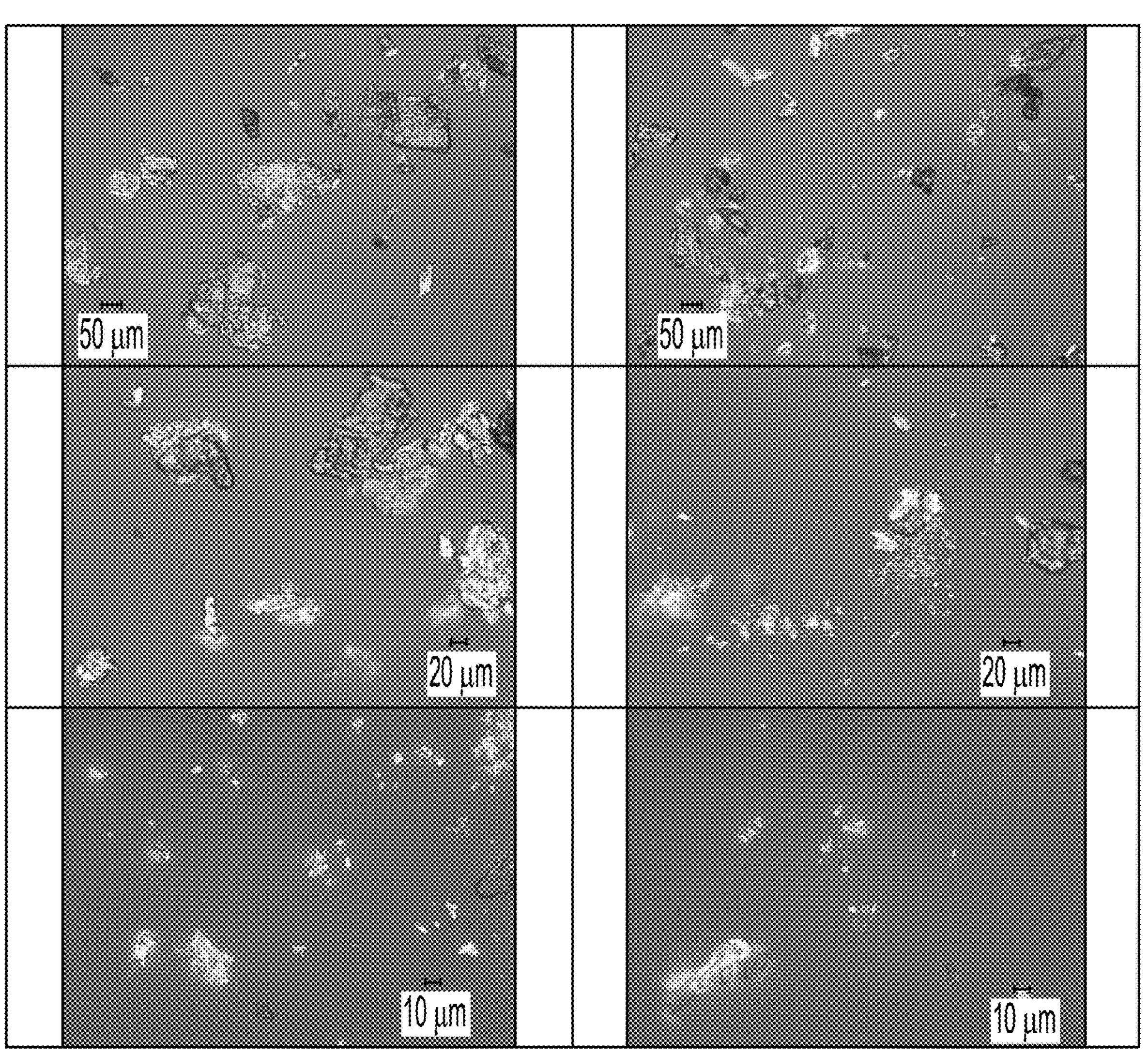
FIG. 16 shows polarized light photomicrographs of a sample of Form I of N,N-DMT.

Solid state heating experiments were conducted starting with Form IV (FIG. 16). As for Form III, these experiments were designed to observe melting and recrystallization behavior at a variety of temperatures and, the approximate melt onset temperature for Form IV (69° C.) from DSC characterization was used as a basis for determining form conversions. Form IV exhibited no changes upon heating at 50° C. for 10 minutes.

V. Stability Experiments to Determine Relative Stability of Forms I, III, and IV Slurry experiments were conducted to determine the relative stability of Forms I, III, and IV. The screening conditions are tabulated at Tables 9-11.

TABLE 9

Stable Form Screen Slurries of N,N-DMT of Form I

| Solvent | Conditions | Observations | XRPD[1] Result |
| --- | --- | --- | --- |
| acetone/water (10:90) | 5° C., 13 d | white solids, fines and aggregates, B/E | Form IV |
| | attempted slurry, RT, 13 d | clear soln. w/brown clear liquid | Form I + minor Form IV |
| cyclohexane | RT, 13 d | white solids, needles/aggregates, B/E | Form I |
| EtOAc/cyclohexane (5:95) | attempted slurry, RT, 13 d | clear soln. w/brown clear liquid | Form I |
| heptane | RT, 13 d | white solids, fines, B/E | Form I |
| | 40° C., 13 d | white solids, thick needles, B/E | Form IV + minor Form I |
| | −20° C., 17 d | white solids, fines, B/E | Form I |

TABLE 9-continued

Stable Form Screen Slurries of N,N-DMT of Form I

| Solvent | Conditions | Observations | XRPD[1] Result |
|---|---|---|---|
| IPA/water (5:95) | attempted slurry, RT, 13 d | clear yellow/orange soln. | — |
| IPA/water (10:90) | 5° C., 13 d | white solids, needles and aggregates, B/E | Form I |
| | attempted slurry, 40° C., 13 d | clear soln. w/brown clear liquid | Form IV + Form III |
| MeOH/water (20:80) | attempted slurry, RT, 13 d | clear soln. w/brown clear liquid | Form IV + minor Form I |
| THF/water (5:95) | attempted slurry, RT, 13 d | clear soln. w/brown clear liquid | Form IV |

[1]Solids from RT slurries were analyzed while damp.

TABLE 10

Stable Form Screen Slurries of N,N-DMT of Form III

| Solvent | Conditions | Observations | XRPD[1] Result |
|---|---|---|---|
| acetone/water (10:90) | attempted slurry, RT, 15 d | yellow oil in soln. | — |
| EtOAc/heptane (5:95) | −20° C., 15 d | white fines, B/E | Form I |
| heptane | RT, 15 d | white solids, fines, B/E | Form I |
| IPAc/heptane (3:97) | RT, 13 d | white solids, fines, B/E | Form IV |
| MeOH/water (20:80) | 5° C., 15 d | white fines, B/E[2] | amorphous |
| — | sample stored at ambient conditions ~2 wks, then observed and reanalyzed | off-white aggregated needles, some B/E | Form I + minor Form III |

[1]Solids from RT slurries were analyzed while damp.
[2]XRPD analyst noted that sample was oily before analysis.

TABLE 11

Stable Form Screen Slurries of N,N-DMT of Form IV

| Solvent | Conditions | Observations | XRPD Result |
|---|---|---|---|
| acetone/water (10:90) | RT, 13 d | off-white solids, fines, B/E | Form IV |
| EtOAc/heptane (5:95) | −20° C., 13 d | off-white solids, fines, B/E | Form IV |
| heptane | RT, 13 d | off-white solids, fines, B/E | Form IV |
| MeOH/water (20:80) | 5° C., 13 d | off-white solids, fines, B/E | Form IV |

In these experiments, saturated solutions containing excess undissolved solids were stirred for extended durations. At these conditions, a metastable form would dissolve at a concentration that is supersaturated with respect to the stable form, causing crystallization of the more stable form over time. Slurries were conducted RT, 40° C., 5° C., and −20° C. for approximately 2 weeks. Solvent systems for which the compound was expected to exhibit limited solubility were employed in an effort to provide suitable conditions for conversion to a more stable form. It should be noted that even with these efforts, a lack of form change does not conclusively determine the stable form and could be attributed to insufficient solubility or time for conversion to a more stable form.

The observed form conversions suggest that Form IV is the most thermodynamically stable polymorph. Form IV also remained unchanged upon slurrying in various solvent systems. All slurry experiments starting with Form III converted to other forms, indicating it is metastable at all conditions tested. Additionally, conversion of Form III to Form I at −20° C. and RT suggests that Form I is likely more stable than Form III within that temperature range. Additionally, Form III exhibited a tendency to crystallize in mixtures with a minor unknown component or other known forms throughout the screen, consistent with its metastable nature.

Since Forms I and IV were identified as two stable forms, further interconversion slurries relative to each other were studied.

VI. Stability Experiments to Determine Relative Stability of Forms III and IV Interconversion slurries were conducted in heptane at RT, −20° C., and 40° C. as in Table 12. In these slurries, the heptane was pre-saturated with N,N-DMT using Form IV solids at the stated temperature, and a portion of the liquid phase was filtered into a mixture of Form I and Form IV solids. A pre-saturated liquid phase is utilized to minimize any kinetic dissolution effects, allowing the less stable (and more soluble) form to dissolve and the most stable (and least soluble) form to precipitate.

TABLE 12

Slurry Competition Studies Between Forms I and IV

| Forms | Starting Materials | | | |
|---|---|---|---|---|
| | Solvent | Conditions | Observations | XRPD Result |
| Form I and Form IV | heptane | RT, 7 d | off-white solids, fines, B/E | Form IV |
| | heptane | −20° C., 7 d | off-white solids, fines, B/E | Form IV |
| | heptane | 40° C., 7 d | off-white solids, fines, B/E | Form IV |

Full conversion to Form IV was observed for all three slurries, indicating it is more stable at those conditions.

VI. Polarized Light Photomicrographs for Forms I and IV

Figure 17:
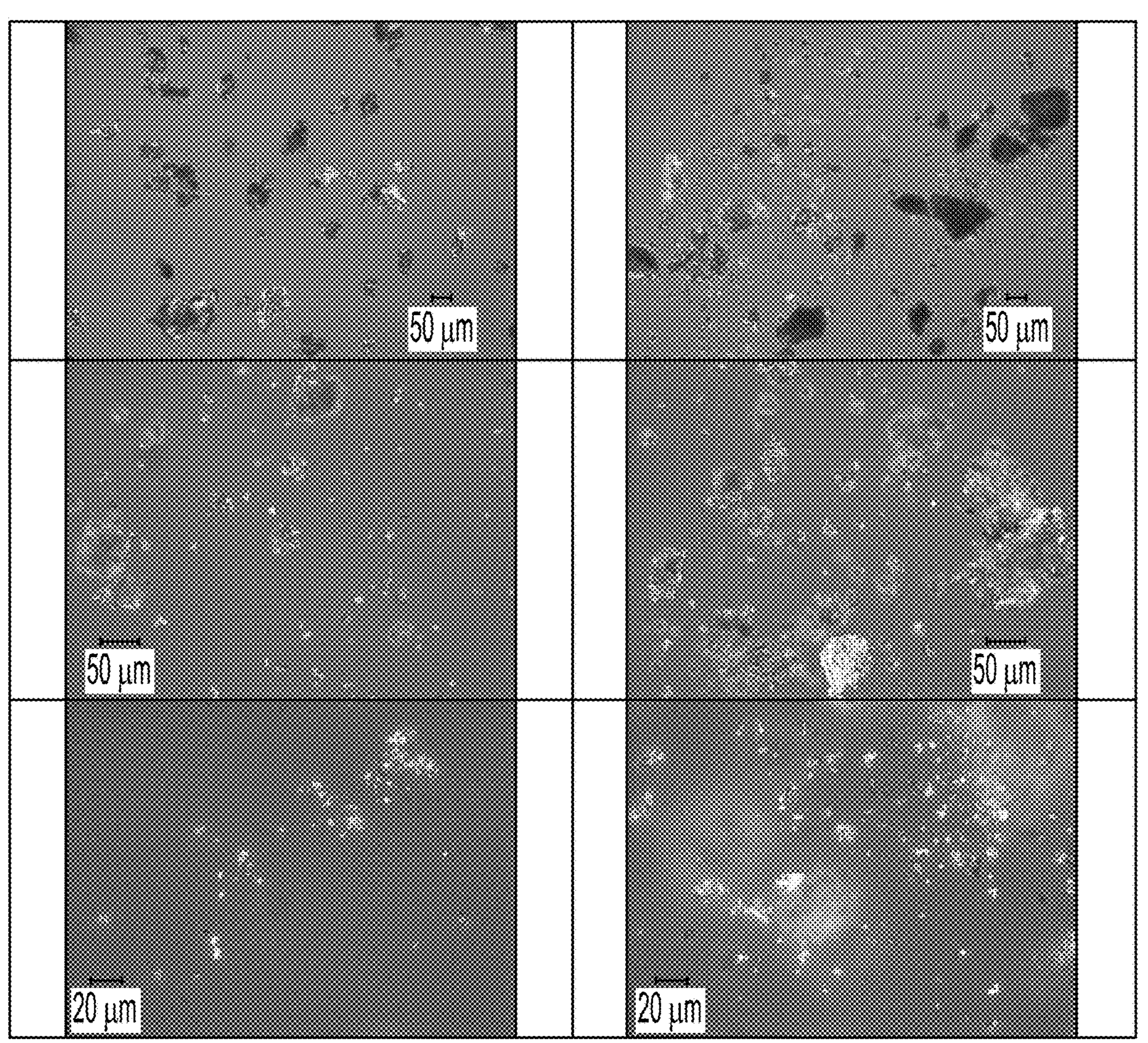
FIG. 17 shows polarized light photomicrographs of a sample of Form IV of N,N-DMT.
Figure 18:
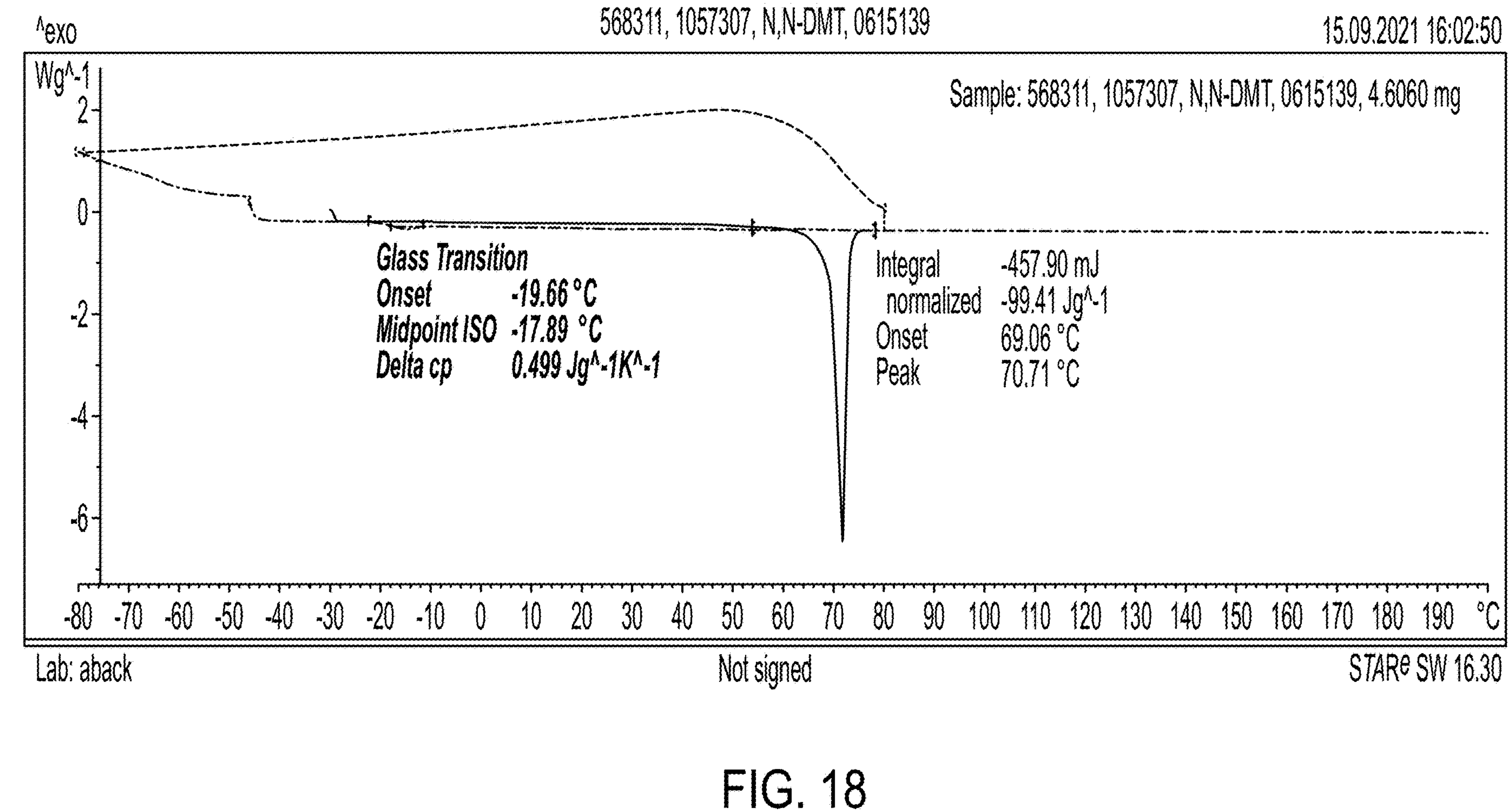
FIG. 18 shows an in situ cycling DSC thermogram of amorphous N,N-DMT starting from a sample of Form IV.

Polarized light microscopy for select forms (Forms I & IV) was performed using a Leica DM LP microscope equipped with a SPOT Insight™ color digital camera. Each sample was placed on a glass slide, a cover glass was placed over the sample, and a drop of mineral oil was added to cover the sample by capillarity. Each sample was observed with crossed polarizers and a first order red compensator. Images were captured using SPOT software (v. 4.5.9). A micron bar was inserted onto each image as a reference for particle size. The photomicrographs are shown in FIG. 17 (Form I) and (Form IV) FIG. 18 displaying agglomerates and individual particles consisting of blades, flakes, and anhedral and drusy particles.

VIII. Amorphous N,N-DMT

Attempts to generate amorphous material did not yield free-flowing amorphous solids, heating/melting experiments were conducted to determine the $T_g$. Observations from a heating/melting experiments indicated that amorphous solids readily crystallize at temperatures spanning −20° C. to 40° C. A cycling DSC experiment was performed to investigate a potential glass transition temperature by preparing amorphous solids in situ, starting with Form IV.

The thermogram is presented in FIG. 19. At the start of the experiment, Form IV solids were heated past the melt (to 80° C.) and held for 10 minutes. The melted material was quickly cooled to −80° C., then reheated to 200° C. A glass transition ($T_g$) is observed as a step in the green curve at −18° ° C. Amorphous materials tend to spontaneously crystallize at temperatures above the $T_g$. Such a low $T_g$ for N,N-DMT is indicative of poor physical stability of amorphous material, particularly at temperatures above −18° C.

IX. Conclusion

The polymorph form, Form IV, identified in this study is found to be the most thermodynamically stable form, and resultantly exhibits a higher melting point than the other known polymorphic forms. On the contrary, the known polymorph, Form I, has been found to be less stable under various conditions (converts to Forms III & Form IV), making it less suitable as an API.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

The invention claimed is:

1. A crystalline Form IV of N,N-dimethyltryptamine, characterized by peaks in an X-ray powder diffraction (XRPD) pattern at 13.6±0.2, 17.8±0.2, and 20.8±0.2° 2θ.

2. The crystalline Form IV of N,N-dimethyltryptamine of claim 1, further characterized by at least one XRPD peak selected from 13.9±0.2, 14.0±0.2, 15.4±0.2, 18.6±0.2, 23.6±0.2, 24.5±0.2, 26.0±0.2, or 26.7=0.2° 2θ.

3. The crystalline Form IV of N,N-dimethyltryptamine of claim 1, further characterized by peaks in an XRPD pattern at 7.7±0.2, 10.4±0.2, 11.9±0.2, 13.0±0.2, 13.9±0.2, 14.0±0.2, 15.2±0.2, 15.4±0.2, 16.2±0.2, 15.4±0.2, 16.2±0.2, 16.9±0.2, 17.5±0.2, 18.1±0.2, 18.6±0.2, 19.3±0.2, 19.8±0.2, 21.1±0.2, 21.6±0.2, 22.4±0.2, 22.7±0.2, 23.6±0.2, 23.8±0.2, 24.5±0.2, 24.8±0.2, 25.2±0.2, 26.1±0.2, 26.7±0.2, 26.9±0.2, 27.5±0.2, 28.0±0.2, 28.2±0.2, 28.6±0.2, 28.8±0.2, 29.3±0.2, 29.5±0.2, 29.6±0.2, 30.2±0.2, 30.4±0.2, 30.6±0.2, 30.9±0.2, 31.1±0.2, 31.6±0.2, 31.9±0.2, 32.8±0.2, 33.2±0.2, 33.7±0.2, 34.5±0.2, and 35.3±0.2° 2θ.

4. The crystalline Form IV of N,N-dimethyltryptamine of claim 1, characterized by an XRPD pattern substantially similar to that shown in FIG. 3.

5. The crystalline Form IV of N,N-dimethyltryptamine of claim 1, which exhibits a Differential Scanning calorimetry (DSC) thermogram comprising an endothermic peak at 70±5° C.

6. The crystalline Form IV of N,N-dimethyltryptamine of claim 1, which exhibits substantially no weight loss at a temperature under 22±5° C. as measured by thermogravimetric (TGA) analysis.

7. The crystalline Form IV of N,N-dimethyltryptamine of claim 1, wherein the crystalline form has a melting point of 69±5° C.

8. A crystalline Form III of N,N-dimethyltryptamine, characterized by peaks in an X-ray powder diffraction (XRPD) pattern at 7.6±0.2 and 15.2±0.2° 2θ.

9. The crystalline Form III of N,N-dimethyltryptamine of claim 8, further characterized by at least one XRPD peak selected from 19.2±0.2, 19.6±0.2, or 23.0±0.2° 2θ.

10. The crystalline Form III of N,N-dimethyltryptamine of claim 8, further characterized by peaks in an XRPD pattern at 16.8±0.2, 19.2±0.2, 19.6±0.2, 20.0±0.2, 20.4±0.2, 20.7±0.2, 21.5±0.2, 22.4±0.2, 22.9±0.2, 23.1±0.2, 26.3±0.2, 27.1±0.2, 27.8±0.2, 28.5±0.2, 30.7±0.2, and 31.6±0.2° 2θ.

11. The crystalline Form III of N,N-dimethyltryptamine of claim 8, characterized by an XRPD pattern substantially similar to that shown in FIG. 2.

12. The crystalline Form III of N,N-dimethyltryptamine of claim 8, which exhibits a Differential Scanning calorimetry (DSC) thermogram comprising an endothermic peak at 44±5° C. when heated at a rate of 10° C./minute.

13. The crystalline Form III of N,N-dimethyltryptamine of claim 8, which exhibits substantially no weight loss at a temperature under 200±5° C. as measured by thermogravimetric (TGA) analysis.

14. The crystalline Form III of N,N-dimethyltryptamine of claim 8, wherein the crystalline form has a melting point of 39±5° C.

15. A pharmaceutical composition comprising the crystalline Form IV of N,N-dimethyltryptamine of claim 1 and a pharmaceutically acceptable excipient.

16. A pharmaceutical composition comprising the crystalline Form III of N,N-dimethyltryptamine of claim 8 and a pharmaceutically acceptable excipient.

17. A method of treating post-traumatic stress disorder (PTSD), depression, or an anxiety disorder in a subject in need thereof, comprising administering the crystalline Form IV of N,N-dimethyltryptamine of claim 1 to the subject.

18. A method of treating post-traumatic stress disorder (PTSD), depression, or an anxiety disorder in a subject in need thereof, comprising administering the crystalline Form III of N,N-dimethyltryptamine of claim 8 to the subject.

* * * * *